(12) United States Patent
Hoffmeyer et al.

(10) Patent No.: US 9,915,631 B2
(45) Date of Patent: Mar. 13, 2018

(54) DISPOSABLE CARTRIDGE FOR MICROFLUIDICS SYSTEM

(71) Applicant: TECAN TRADING AG, Mannedorf (CH)

(72) Inventors: Daniel Hoffmeyer, San Jose, CA (US); Tiffany Lay, San Jose, CA (US); Travis Lee, San Francisco, CA (US)

(73) Assignee: Tecan Trading AG, Mannedorf (CH)

( * ) Notice: Subject to any disclaimer, the term of this patent is extended or adjusted under 35 U.S.C. 154(b) by 810 days.

(21) Appl. No.: 14/361,556

(22) PCT Filed: Jan. 6, 2014

(86) PCT No.: PCT/EP2014/050085
§ 371 (c)(1),
(2) Date: May 29, 2014

(87) PCT Pub. No.: WO2014/108366
PCT Pub. Date: Jul. 17, 2014

(65) Prior Publication Data
US 2014/0353157 A1 Dec. 4, 2014

(30) Foreign Application Priority Data
Jan. 9, 2013 (WO) ............... PCT/EP2013/050326

(51) Int. Cl.
*G01N 27/447* (2006.01)
*B01L 3/00* (2006.01)
*B81B 1/00* (2006.01)

(52) U.S. Cl.
CPC ........ *G01N 27/44791* (2013.01); *B01L 3/505* (2013.01); *B01L 3/502715* (2013.01);
(Continued)

(58) Field of Classification Search
CPC ............... B01L 3/502715; B01L 3/505; B01L 3/502792; B01L 2200/025;
(Continued)

(56) References Cited

U.S. PATENT DOCUMENTS

| | | | |
|---|---|---|---|
| 5,486,337 A | 1/1996 | Ohkawa et al. | |
| 6,565,727 B1 | 5/2003 | Shenderov | |
| 2009/0298059 A1 | 12/2009 | Gumbrecht et al. | |

FOREIGN PATENT DOCUMENTS

| | | |
|---|---|---|
| WO | WO 2006/125767 | 11/2006 |
| WO | WO 2008/106678 | 9/2008 |

(Continued)

*Primary Examiner* — Gurpreet Kaur
(74) *Attorney, Agent, or Firm* — Notaro, Michalos & Zaccaria P.C.

(57) ABSTRACT

A digital microfluidics system for manipulating samples in liquid droplets within a gap between a first hydrophobic surface of a bottom layer and a second hydrophobic surface of at least one disposable cartridge. Disposable cartridges comprise a body and/or a rigid cover plate. The bottom layer of each disposable cartridge is a flexible film that is sealingly attached to the body or plate. The cartridge has no spacer between the first and second hydrophobic surfaces. When using these cartridges, the bottom layers configured as a working film for manipulating samples in liquid droplets thereon, is placed on an electrode array of a digital microfluidics system. The array has individual electrodes. The digital microfluidics system also comprises a central control unit for controlling the selection of the individual electrodes of the electrode array and for providing these electrodes with individual voltage pulses for manipulating liquid droplets by electrowetting.

48 Claims, 7 Drawing Sheets

Figure 1:
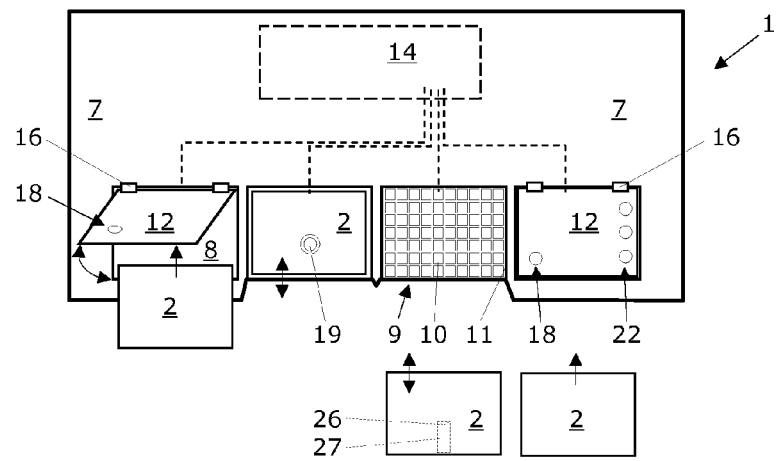

(52) U.S. Cl.
CPC .. *B01L 3/502792* (2013.01); *G01N 27/44756* (2013.01); *B01L 2200/027* (2013.01); *B01L 2200/04* (2013.01); *B01L 2300/044* (2013.01); *B01L 2300/123* (2013.01); *B01L 2400/0427* (2013.01); *B81B 1/00* (2013.01)

(58) Field of Classification Search
CPC ....... B01L 2200/027; B01L 2200/0673; B01L 2300/043; B01L 2300/044; B01L 2300/089; B01L 2300/123
See application file for complete search history.

(56) References Cited

FOREIGN PATENT DOCUMENTS

| WO | WO2009137415 | 11/2009 |
|---|---|---|
| WO | WO2010009463 | 1/2010 |
| WO | WO 2010/069977 | 6/2010 |
| WO | WO 2011/002957 | 1/2011 |

DISPOSABLE CARTRIDGE FOR MICROFLUIDICS SYSTEM

RELATED PATENT APPLICATIONS

The present application claims priority of the international patent application PCT/EP2013/050326, filed on 9 Jan. 2013, the entire content of which being herein incorporated by explicit reference for all purposes.

FIELD OF TECHNOLOGY

The present invention relates to a disposable cartridge that can be used in or on digital microfluidics systems for manipulating samples in liquid droplets. The digital microfluidics systems comprise an electrode array supported by a substrate, and a central control unit for controlling the selection of individual electrodes of this electrode array and for providing them with individual voltage pulses for manipulating liquid droplets by electrowetting. The invention also relates to a digital microfluidics system for facilitating droplet actuated molecular techniques and to an alternative method for manipulating samples in liquid droplets digital in a microfluidics system or device.

RELATED PRIOR ART

Automated liquid handling systems are generally well known in the art. An example is the Freedom EVO® robotic workstation from the present applicant (Tecan Schweiz AG, Seestrasse 103, CH-8708 Männedorf, Switzerland). This device enables automated liquid handling in a stand-alone instrument or in automated connection with an analytical system. These automated systems typically require larger volumes of liquids (microliter to milliliter) to process. They are also larger systems that are not designed to be portable.

Many approaches to deal with the automated processing of biological samples originate from the field of microfluidics. This technical field generally relates to the control and manipulation of liquids in a small volume, usually in the micro- or nanoscale format. Liquid movement in a channel system is known per se as, e.g. being controlled by micro pumps in stationary devices or centripetal forces in rotating labware. In digital microfluidics, a defined voltage is applied to electrodes of an electrode array, so that individual droplets are addressed (electrowetting).

For a general overview of the electrowetting method, please see Washizu, IEEE Transactions on Industry Applications, Volume 34, No. 4, 1998, and Pollack et al., *Lab chip*, 2002, Volume 2, 96-101. Briefly, electrowetting refers to a method to move liquid droplets using arrays of microelectrodes, preferably covered by a hydrophobic layer. By applying a defined voltage to electrodes of the electrode array, a change of the surface tension of the liquid droplet, which is present on the addressed electrodes, is induced. This results in a remarkable change of the contact angle of the droplet on the addressed electrode, hence in a movement of the droplet. For such electrowetting procedures, two principle ways to arrange the electrodes are known: using one single surface with an electrode array for inducing the movement of droplets or adding a second surface that is opposite a similar electrode array and that provides at least one ground electrode. A major advantage of the electrowetting technology is that only a small volume of liquid is required, e.g. a single droplet. Thus, liquid processing can be carried out within considerably shorter time. Furthermore the control of the liquid movement can be completely under electronic control resulting in automated processing of samples.

A device for liquid droplet manipulation by electrowetting using one single surface with an electrode array (a monoplanar arrangement of electrodes) is known from the U.S. Pat. No. 5,486,337. All electrodes are placed on a surface of a carrier substrate, lowered into the substrate, or covered by a non-wettable surface. A voltage source is connected to the electrodes. The droplet is moved by applying a voltage to subsequent electrodes, thus guiding the movement of the liquid droplet above the electrodes according to the sequence of voltage application to the electrodes.

An electrowetting device for microscale control of liquid droplet movements, using an electrode array with an opposing surface with at least one ground electrode is known from U.S. Pat. No. 6,565,727 (a biplanar arrangement of electrodes). Each surface of this device may comprise a plurality of electrodes. The drive electrodes of the electrode array are preferably arranged in an interdigitated relationship with each other by projections located at the edges of each single electrode. The two opposing arrays form a gap. The surfaces of the electrode arrays directed towards the gap are preferably covered by an electrically insulating, hydrophobic layer. The liquid droplet is positioned in the gap and moved within a non-polar filler fluid by consecutively applying a plurality of electric fields to a plurality of electrodes positioned on the opposite sites of the gap.

Containers with a polymer film for manipulating samples in liquid droplets thereon are known from WO 2010/069977 A1: A biological sample processing system comprises a container for large volume processing and a flat polymer film with a lower surface and a hydrophobic upper surface. The flat polymer film is kept at a distance to a base side of the container by protrusions. This distance defines at least one gap when the container is positioned on the film. A liquid droplet manipulation instrument comprises at least one electrode array for inducing liquid droplet movements. A substrate supporting the at least one electrode array is also disclosed as well as a control unit for the liquid droplet manipulation instrument. The container and the film are reversibly attached to the liquid droplet manipulation instrument. The system thus enables displacement of at least one liquid droplet from the at least one well through the channel of the container onto the hydrophobic upper surface of the flat polymer film and above the at least one electrode array. The liquid droplet manipulation instrument is accomplished to control a guided movement of said liquid droplet on the hydrophobic upper surface of the flat polymer film by electrowetting and to process there the biological sample.

The use of such an electrowetting device for manipulating liquid droplets in the context of the processing of biological samples is also known from the international patent application published as WO 2011/002957 A2. There, it is disclosed that a droplet actuator typically includes a bottom substrate with the control electrodes (electrowetting electrodes) insulated by a dielectric, a conductive top substrate, and a hydrophobic coating on the bottom and top substrates. Also disclosed are droplet actuator devices for replacing one or more components of a droplet actuator, i.e. disposable components that may be readily replaced (such as movable films, reversibly attachable top and bottom substrates, and self-contained replaceable cartridges).

From the international application published as WO 2011/002957 A2, droplet actuators with a fixed bottom substrate (e.g. of a PCB), with electrowetting electrodes, and with a removable or replaceable top substrate are known. A self-containing cartridge may e.g. include buffers, reagents, and filler fluid. Pouches in the cartridge may be used as fluid reservoirs and may be punctured to release fluid (e.g. a reagent or oil) into a cartridge gap. The cartridge may include a ground electrode, which may be replaced by a hydrophobic layer, and an opening for loading samples into the gap of the cartridge. Interface material (e.g. a liquid, glue or grease) may provide adhesion of the cartridge to the electrode array.

Disposable cartridges for microfluidic processing and analysis in an automated system for carrying out molecular diagnostic analysis are disclosed in WO 2006/125767 A1 (see US 2009/0298059 A1 for an English translation). The cartridge is configured as a flat chamber device (with about the size of a check card) and can be inserted into the system. A sample can be pipetted into the cartridge through a port.

Droplet actuator structures are known from the international patent application WO 2008/106678. This document particularly refers to various wiring configurations for electrode arrays of droplet actuators, and additionally discloses a two-layered embodiment of such a droplet actuator which comprises a first substrate with a reference electrode array separated by a gap from a second substrate comprising control electrodes. The two substrates are arranged in parallel, thereby forming the gap. The height of the gap may be established by spacer. A hydrophobic coating is in each case disposed on the surfaces which face the gap. The first and second substrate may take the form of a cartridge, eventually comprising the electrode array.

OBJECTS AND SUMMARY OF THE PRESENT INVENTION

It is an object of the present invention to suggest an alternative disposable cartridge for use in or on digital microfluidics systems or digital microfluidics devices which are configured to accommodate one or more disposable cartridges for manipulating samples in liquid droplets.

This object is achieved in that a first alternative disposable cartridge is provided. The first alternative cartridge of the present invention comprises:
(a) a body with at least one compartment configured to hold therein processing liquids, reagents or samples, at least one of said compartments comprising a through hole for delivering at least some of its content;
(b) a bottom layer with a first hydrophobic surface that is impermeable to liquids and that is configured as a working film for manipulating samples in liquid droplets thereon utilizing an electrode array of a digital microfluidics system when the bottom layer of the disposable cartridge is placed over said electrode array;
(c) a top layer with a second hydrophobic surface that is attached to a lower surface of the body of the disposable cartridge; and
(d) a gap that is located between the first hydrophobic surface of the bottom layer and the second hydrophobic surface of the top layer.

Optionally, the second hydrophobic surface provided by the top layer may be or may be not impermeable to liquids, it is preferred however that the second hydrophobic surface or the top layer respectively is at least permeable to ions.

The first alternative disposable cartridge of the present invention is characterized in that the bottom layer is configured as a flexible film that is sealingly attached to the top layer along a circumference of the flexible bottom layer, the disposable cartridge thus being devoid of a spacer that is located between the flexible bottom layer and the top layer for defining a particular distance between said first hydrophobic surface and said second hydrophobic surface. The first alternative disposable cartridge of the present invention is further characterized in that the top layer is configured to provide a seal between a lower end of at least one compartment and the gap, the top layer comprising loading sites for transferring processing liquids, reagents or samples into the gap.

This object is achieved in that a second alternative disposable cartridge is provided. The second alternative disposable cartridge of the present invention comprises:
(a) a body with a lower surface, an upper surface, and at least one through hole;
(b) a bottom layer with a first hydrophobic surface that is impermeable to liquids and that is configured as a working film for manipulating samples in liquid droplets thereon utilizing an electrode array of a digital microfluidics system when the bottom layer of the disposable cartridge is placed over said electrode array;
(c) an electrically conductive material attached to the lower surface of the body, the electrically conductive material being configured to provide the lower surface of the body with a second hydrophobic surface; and
(d) a gap that is located between the first hydrophobic surface of the bottom layer and the second hydrophobic surface of the electrically conductive material.

Optionally, the electrically conductive material that provides the body with the second hydrophobic surface may be or may be not impermeable to liquids, it is preferred however that the electrically conductive material that provides the second hydrophobic surface is at least permeable to ions.

The second alternative disposable cartridge of the present invention is characterized in that the bottom layer is configured as a flexible film that is sealingly attached to the electrically conductive material of the disposable cartridge along a circumference of the flexible bottom layer, the disposable cartridge thus being devoid of a spacer that is located between the flexible bottom layer and the electrically conductive material for defining a particular distance between said first hydrophobic surface and said second hydrophobic surface. The second alternative disposable cartridge of the present invention is further characterized in that the at least one through hole of the body is configured as a loading site for transferring processing liquids, reagents or samples into the gap.

It is a further object of the present invention to suggest a microfluidics system or device into or onto which one or more such disposable cartridges for manipulating samples in liquid droplets therein can be placed. This object is achieved in that a first and second alternative digital microfluidics system is provided. The first and second digital microfluidics system for manipulating samples in liquid droplets within a gap between a first hydrophobic surface of a bottom layer and a second hydrophobic surface of at least one disposable cartridge of the present invention comprises:
(a) a base unit with at least one cartridge accommodation site that is configured for taking up one disposable cartridge;
(b) an electrode array located at said at least one cartridge accommodation site of the base unit, the electrode array being supported by a bottom substrate and substantially extending in a first plane and comprising a number of individual electrodes;
(c) a central control unit for controlling the selection of the individual electrodes of said electrode array and for providing these electrodes with individual voltage pulses for manipulating liquid droplets within the gap of said cartridge by electrowetting;

(d) a number of suction holes that penetrate the electrode array and/or the bottom substrate and that are located at the at least one cartridge accommodation site of the base unit;

(e) a vacuum source for establishing an underpressure in an evacuation space; and (f) a number of vacuum lines that link the suction holes to the vacuum source.

The first digital microfluidics system of the present invention is further characterized in that a gasket, when a disposable cartridge is located at the at least one cartridge accommodation site, seals in said cartridge accommodation site the evacuation space, which is defined by a flexible bottom layer of a disposable cartridge, an uppermost surface of the cartridge accommodation site, and the gasket. The digital microfluidics system of the present invention is further characterized in that the underpressure in the evacuation space causes the flexible bottom layer of the disposable cartridge that is placed at the cartridge accommodation site to be attracted and spread over the uppermost surface of the cartridge accommodation site of the digital microfluidics system without the use of a spacer that is located in the gap between the first hydrophobic surface of the flexible bottom layer and the second hydrophobic surface of the at least one disposable cartridge.

The second alternative digital microfluidics system of the present invention is characterized in that the digital microfluidics system comprises a spacer for defining a particular distance between said first hydrophobic surface and said second hydrophobic surface and a frame for centering a disposable cartridge at said cartridge accommodation site, for holding down the disposable cartridge to the spacer, and for sealing an evacuation space by first and second seals of the frame. The microfluidics system further comprises an evacuation space, which is defined by a flexible bottom layer of a disposable cartridge, an uppermost surface of the cartridge accommodation site, and the frame with the seals. The digital microfluidics system of the present invention is further characterized in that the underpressure in the evacuation space causes the flexible bottom layer that is placed at the cartridge accommodation site to be attracted to and spread over the uppermost surface of the cartridge accommodation site of the digital microfluidics system.

Preferably, the seals are of two different types, comprising i.e. a different material and/or cross section. A number of first type seals being of a very compliant material or being configured as a lip seal. The first type seals preferably are capable to be largely deformed allowing the seal bearing parts to be firmly pressed against respective counter parts. Preferred materials for this compliant seal are e.g. O-rings of natural rubber or of a DuPont Elastomer such as Neoprene®. A second seal type preferably is of a material that is less compliant and stiff enough to undergo only a minimal compression and thus combining the task of effectively sealing the evacuation space and of pressing the disposable cartridge firmly against the spacer. Preferred materials for this stiff seal are e.g. O-rings of a DuPont Performance Elastomer such as Viton®.

It is yet a further object of the present invention to suggest an alternative method for manipulating samples in liquid droplets digital in a digital microfluidics system or device. This further object is achieved in that a first alternative method for manipulating samples in liquid droplets that adhere to a hydrophobic surface of a working film is proposed. The first alternative method according to the present invention comprises the steps of:

(a) providing a disposable cartridge with a first hydrophobic surface of a bottom layer, with a second hydrophobic surface of a top layer, and with a gap between the first and second hydrophobic surfaces, the disposable cartridge further comprising a body with at least one compartment to therein hold processing liquids, reagents or samples, said compartment comprising a through hole for delivering at least some of its content to the gap;

(b) providing a digital microfluidics system with an electrode array that substantially extends in a first plane and that comprises a number of individual electrodes supported by a bottom substrate and connected to a central control unit of the digital microfluidics system for controlling the selection of individual electrodes of said electrode array and for providing these electrodes with individual voltage pulses for manipulating said liquid droplets on said first hydrophobic surface by electrowetting; and (c) defining the gap so that the hydrophobic surface of the top layer extends substantially parallel to and in a distance to said first hydrophobic surface of the bottom layer.

The first alternative method for manipulating samples in liquid droplets of the present invention is characterized in that the method further comprises the steps of:

(d) providing the bottom layer as a flexible film that is sealingly attached to the top layer along a circumference of the flexible bottom layer, the disposable cartridge thus being devoid of a spacer that is located between the flexible bottom layer and the top layer for defining a particular distance between said first hydrophobic surface and said second hydrophobic surface;

(e) placing the disposable cartridge on a cartridge accommodation site of a base unit of the digital microfluidics system, the top layer being configured to provide a seal between a lower end of at least one compartment and the gap, and the top layer comprising loading sites for transferring processing liquids, reagents or samples into the gap;

(f) sealing in the cartridge accommodation site an evacuation space by a gasket located around a circumference of the cartridge accommodation site, the evacuation space being defined by the flexible bottom layer, the electrode array, the bottom substrate, and the gasket; and (g) creating in the evacuation space an underpressure, which causes the flexible bottom layer of the disposable cartridge that is placed on the cartridge accommodation site to be attracted and spread over the electrode array and bottom substrate.

This further object is achieved in that a second alternative method for manipulating samples in liquid droplets that adhere to a hydrophobic surface of a working film is proposed. The second alternative method according to the present invention comprises the steps of:

(a) providing a disposable cartridge with a body comprising a lower surface, an upper surface, at least one through hole, and a bottom layer with a first hydrophobic surface; an electrically conductive material being attached to the lower surface of the body, the electrically conductive material at least being permeable to ions and configured to provide the lower surface of the body with a second hydrophobic surface; a gap being provided between the first and second hydrophobic surfaces;

(b) providing a digital microfluidics system with an electrode array that substantially extends in a first plane and that comprises a number of individual electrodes supported by a bottom substrate and connected to a central control unit of the digital microfluidics system for controlling the selection of individual electrodes of said electrode array and for providing these electrodes with individual voltage pulses for manipulating said liquid droplets on said first hydrophobic surface by electrowetting; and (c) defining the gap so that the first and second hydrophobic surfaces extend substantially parallel and in a distance to each other; the at least one through hole of the body being configured as a loading site for transferring processing liquids, reagents or samples into the gap.

The second alternative method for manipulating samples in liquid droplets of the present invention is characterized in that the method further comprises the steps of:

(d) providing the bottom layer as a flexible film that is sealingly attached to the electrically conductive material along a circumference of the flexible bottom layer, the disposable cartridge thus being devoid of a spacer that is located between the first and second hydrophobic surfaces for defining a particular distance between said first hydrophobic surface and said second hydrophobic surface;

(e) placing the disposable cartridge on a cartridge accommodation site of a base unit of the digital microfluidics system;

(f) sealing in the cartridge accommodation site an evacuation space by a gasket located around a circumference of the cartridge accommodation site, the evacuation space being defined by the flexible bottom layer, the electrode array, the bottom substrate, and the gasket; and (g) creating in the evacuation space an underpressure, which causes the flexible bottom layer of the disposable cartridge that is placed on the cartridge accommodation site to be attracted and spread over the electrode array and bottom substrate.

This further object is achieved in that a third and fourth alternative method for manipulating samples in liquid droplets that adhere to a hydrophobic surface of a working film is proposed. The third alternative method according to the present invention comprises the steps of:

(a) providing a disposable cartridge with a first hydrophobic surface of a bottom layer, with a second hydrophobic surface, and with a gap between the first and second hydrophobic surfaces, the disposable cartridge further comprising a body and/or a plane rigid cover plate, and at least one through hole for delivering processing liquids, reagents or samples to the gap;

(b) providing a digital microfluidics system with at least one electrode array that substantially extends in a first plane and that comprises a number of individual electrodes supported by a bottom substrate and connected to a central control unit of the digital microfluidics system for controlling the selection of individual electrodes of said electrode array and for providing these electrodes with individual voltage pulses for manipulating said liquid droplets on said first hydrophobic surface by electrowetting; and (c) defining the gap so that the hydrophobic surface extends substantially parallel to and in a distance to said first hydrophobic surface of the bottom layer.

The third alternative method for manipulating samples in liquid droplets of the present invention is characterized in that the method further comprises the steps of:

(d) providing the bottom layer as a flexible film that is sealingly attached to the body or the plane rigid cover plate of the disposable cartridge along a circumference of the flexible bottom layer, the disposable cartridge thus being devoid of a spacer that is located in the gap for defining a particular distance between said first hydrophobic surface and said second hydrophobic surface;

(e) placing the disposable cartridge at a cartridge accommodation site of a base unit of the digital microfluidics system;

(f) sealing in the cartridge accommodation site an evacuation space by a gasket, the evacuation space being defined by the flexible bottom layer of the disposable cartridge, the uppermost surface of the cartridge accommodation site and the gasket; and (g) creating in the evacuation space an underpressure, which causes the flexible bottom layer of the disposable cartridge that is placed on the cartridge accommodation site to be attracted and spread over the uppermost surface of the cartridge accommodation site.

The fourth alternative method for manipulating samples in liquid droplets of the present invention is characterized in that the method further comprises the steps of:

(d) providing the bottom layer as a flexible film that is sealingly attached to the plane rigid cover plate of the disposable cartridge along a circumference of the flexible bottom layer, the disposable cartridge thus being devoid of a spacer that is located in the gap for defining a particular distance between said first hydrophobic surface and said second hydrophobic surface;

(e) placing the disposable cartridge within a centering frame at a cartridge accommodation site and on a spacer of a base unit of the digital microfluidics system;

(f) applying pressure on the disposable cartridge in the cartridge accommodation site and sealing an evacuation space by first and second seals of the frame, the evacuation space being defined by the flexible bottom layer of the disposable cartridge, the uppermost surface of the cartridge accommodation site, and the frame with the seals; and (g) creating in the evacuation space an underpressure, which causes the flexible bottom layer of the disposable cartridge that is placed on the cartridge accommodation site to be attracted and spread over the uppermost surface of the cartridge accommodation site.

Additional and inventive features and preferred embodiments and variants of the digital microfluidics system, the disposable cartridge, and the method for manipulating samples in liquid droplets derive from the respective dependent claims.

Advantages of the present invention comprise:

According to one embodiment, a gasket between the cartridge and the PCB of the digital microfluidics system together with the geometry of the cartridge, the flexible bottom layer and an underpressure applied to the underside of this flexible bottom layer is sufficient to define the gap between the two films that enclose the gap.

According to another embodiment, a spacer between the cartridge and the PCB of the digital microfluidics system together with the geometry of the cartridge, the flexible bottom layer, a frame with seals and an underpressure applied to the underside of this flexible bottom layer is sufficient to define the gap between the two films that enclose the gap.

The disposable cartridge of the present invention does not need a spacer between the two surfaces that enclose the gap where the electrowetting takes place.

The gasket can be a part of the disposable cartridge or can be fixed to the surface of the PCB.

The spacer preferably is a part of the PCB.

BRIEF INTRODUCTION OF THE DRAWINGS

Figure 2:
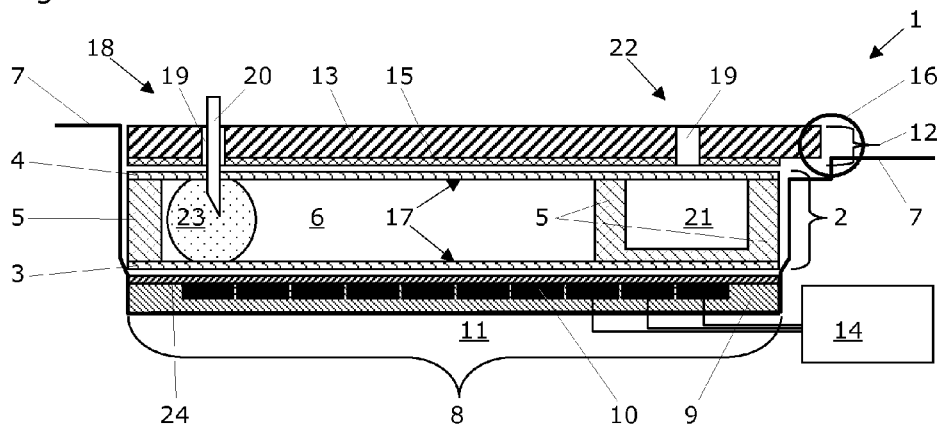
Figure 3:
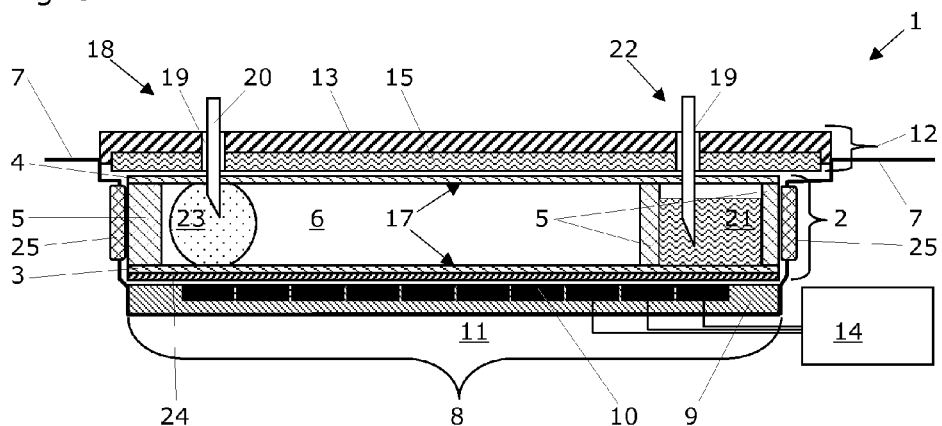
Figure 4A:
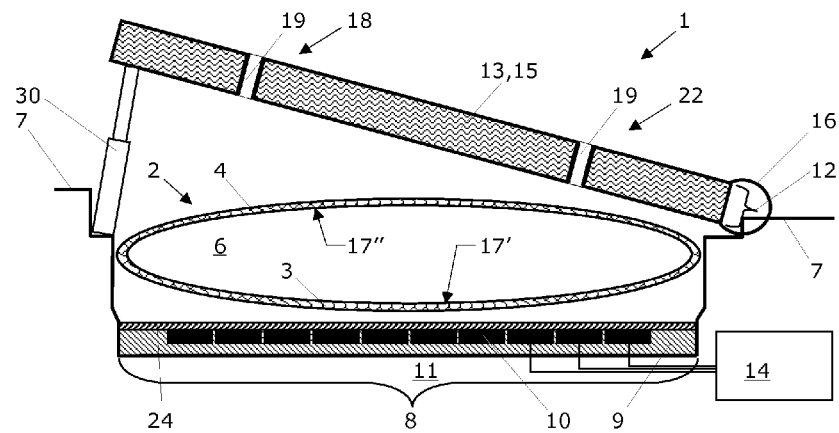
Figure 4B:
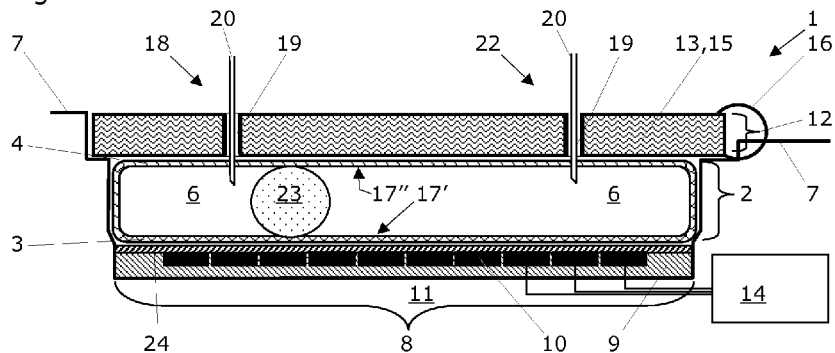
Figure 5:
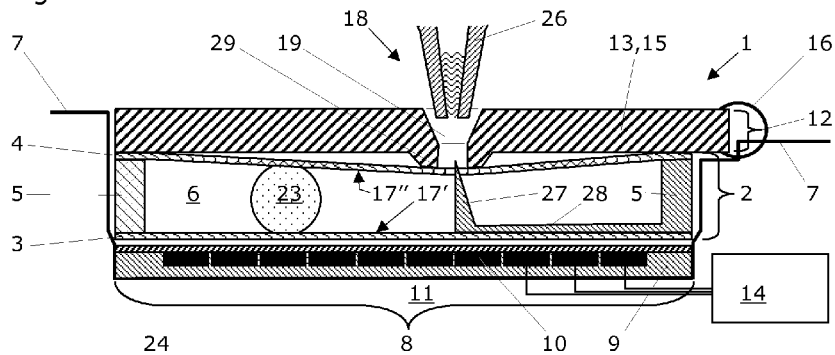
Figure 6:
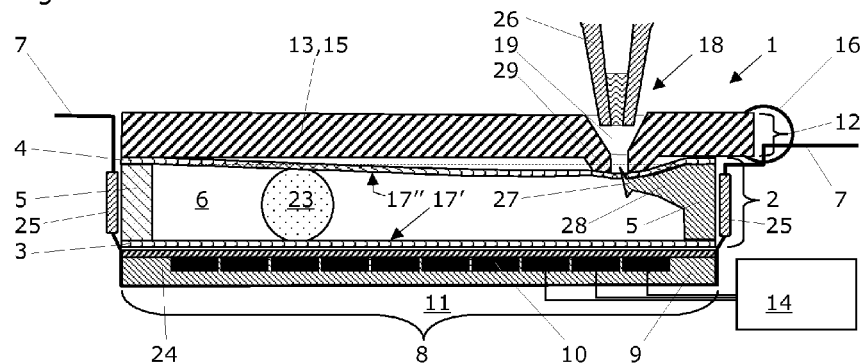
Figure 7:
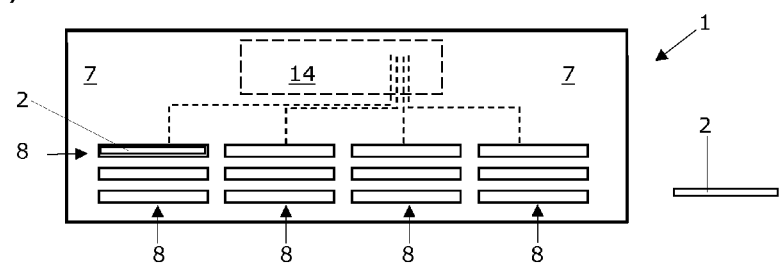
Figure 8A:
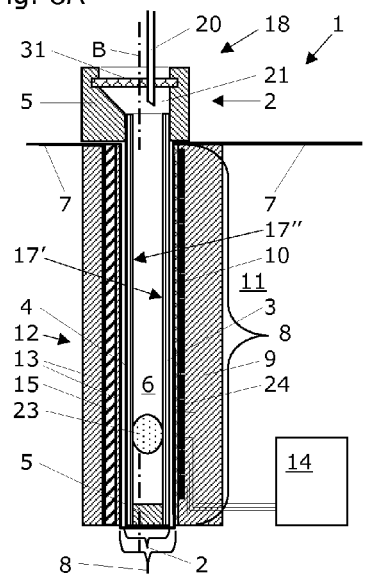
Figure 8B:
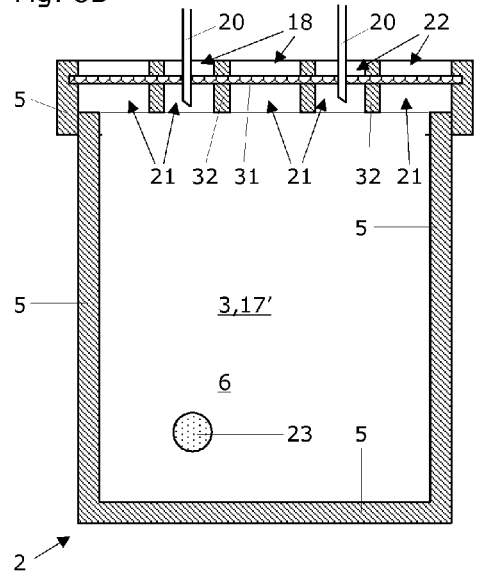
Figure 9:
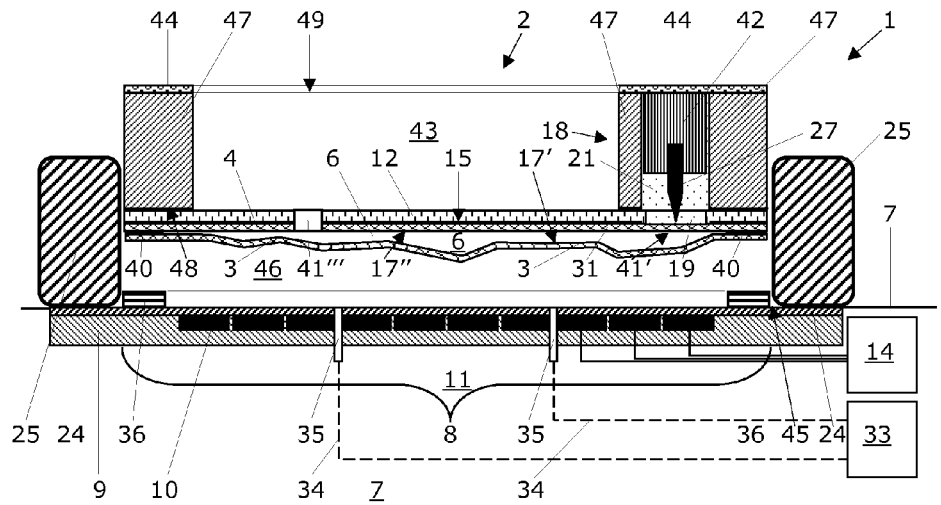
Figure 10:
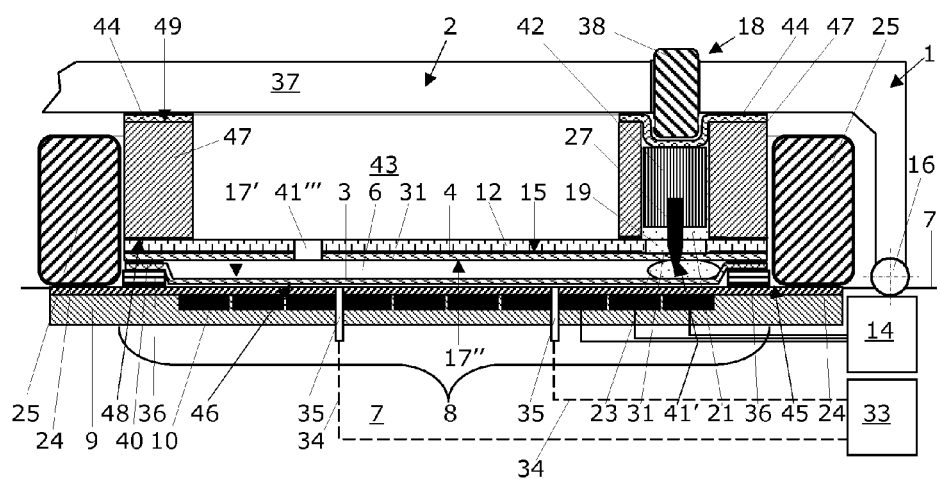
Figure 11:
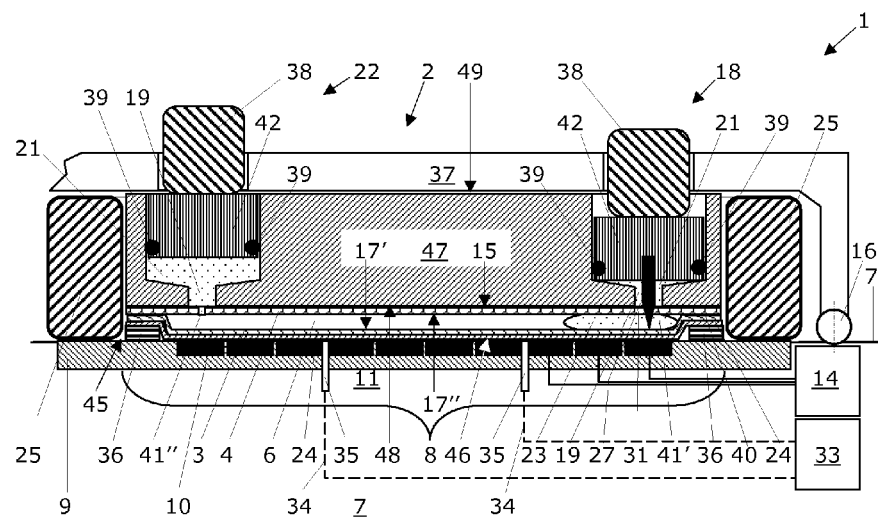
Figure 12:
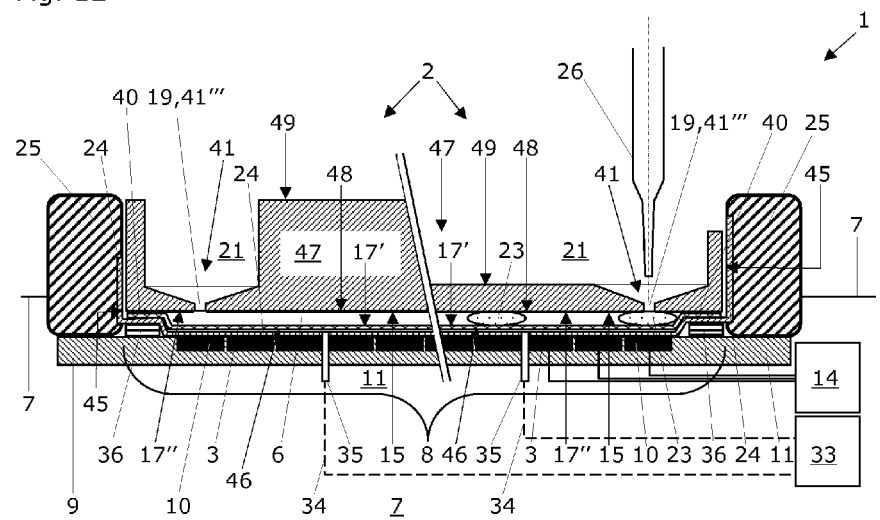
Figure 13:
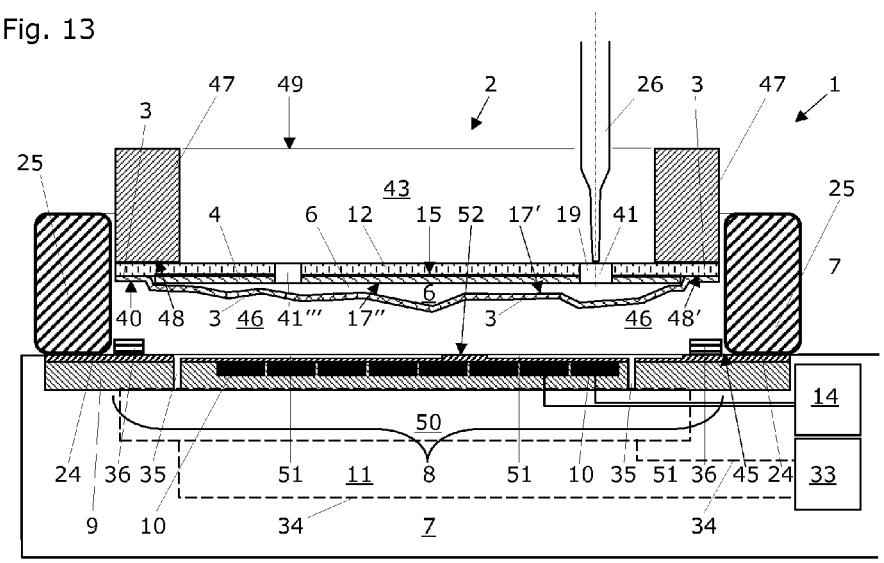
Figure 14:
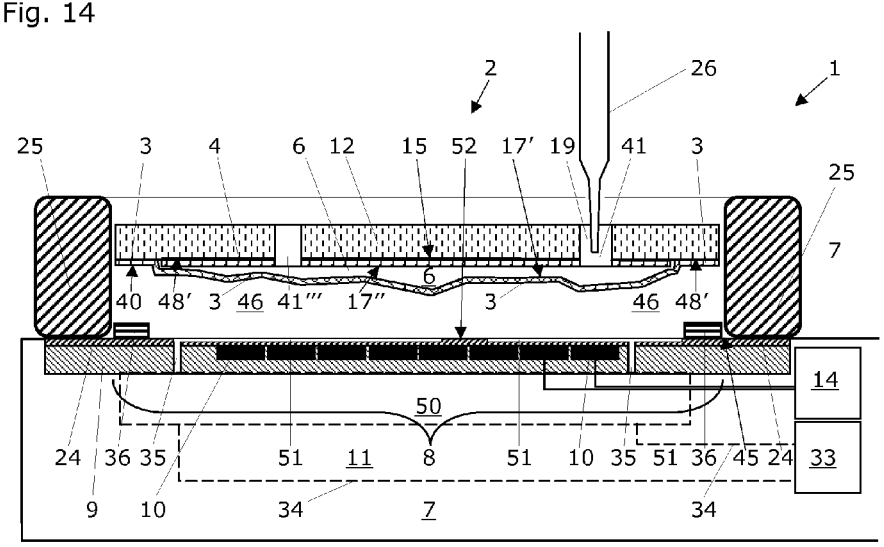
Figure 15:
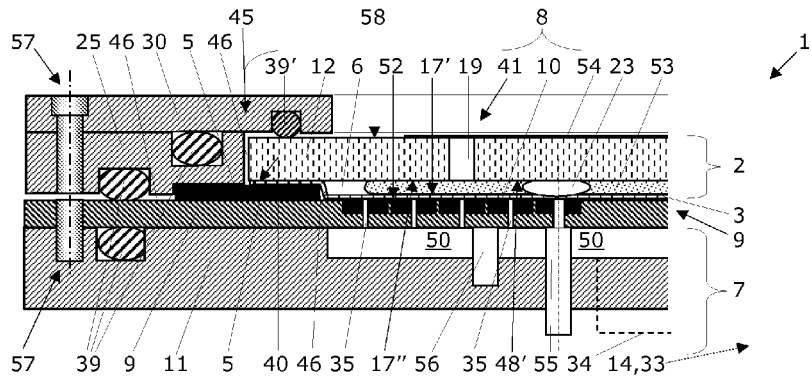
Figure 16:
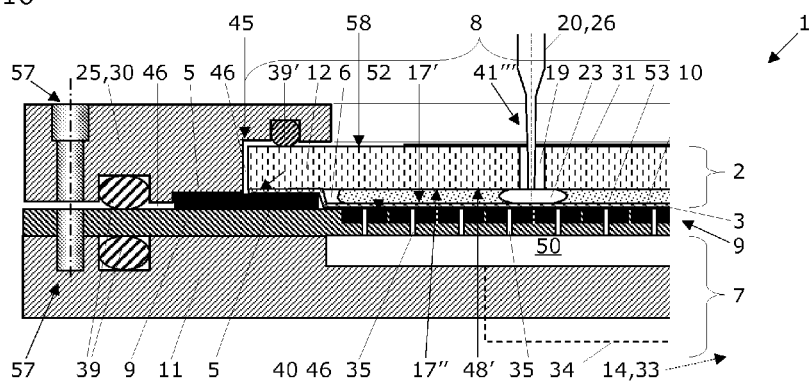
Figure 17:
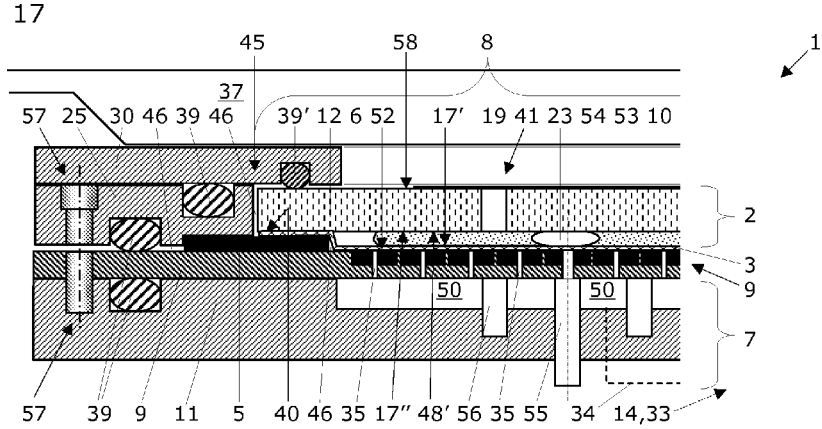

The self-contained disposable cartridge, the digital microfluidics system, and the method for manipulating samples according to the present invention are explained with the help of the attached schematic drawings that show selected and exemplary embodiments of the present invention without narrowing the scope and gist of this invention. It is shown in:

FIG. 1 an overview over a digital microfluidics system that is equipped with a central control unit and a base unit, with four cartridge accommodation sites that each comprise an electrode array, and a movable cover plate;

FIG. 2 a section view of one cartridge accommodation site with a disposable cartridge according to a first embodiment accommodated therein;

FIG. 3 a section view of one cartridge accommodation site with a disposable cartridge according to a second embodiment accommodated therein;

FIG. 4 section views of one cartridge accommodation site with a disposable cartridge according to a third embodiment accommodated therein, wherein:

FIG. 4A shows the cushion-like cartridge as laid into a cartridge accommodation site with a partly closed cover, and FIG. 4B shows the cushion-like cartridge as pressed into operation shape inside the cartridge accommodation site by the entirely closed cover;

FIG. 5 a section view of one cartridge accommodation site with a disposable cartridge according to a fourth embodiment accommodated therein;

FIG. 6 a section view of one cartridge accommodation site with a disposable cartridge according to a fifth embodiment accommodated therein;

FIG. 7 an overview over a digital microfluidics system that is equipped with a central control unit and a base unit, with twelve cartridge accommodation sites that each comprise an electrode array and a fixed cover plate;

FIG. 8 section views of one cartridge accommodation site with a disposable cartridge according to a sixth embodiment accommodated therein, wherein:

FIG. 8A shows a top-entry cartridge inserted into a substantially vertical cartridge accommodation site with a substantially vertical electrode array and cover plate, and FIG. 8B shows the top-entry cartridge as viewed from the section plane B indicated in FIG. 8A;

FIG. 9 a section view of one disposable cartridge before reaching its accommodation site, the disposable cartridge being configured according to a seventh embodiment;

FIG. 10 a section view of the disposable cartridge of FIG. 9 after reaching its accommodation site, the disposable cartridge being configured according to a seventh embodiment and being hold in place by a clamp;

FIG. 11 a section view of a disposable cartridge after reaching its accommodation site, the disposable cartridge being configured according to an eighth embodiment and being hold in place by a clamp;

FIG. 12 a section view of a disposable cartridge after reaching its accommodation site, the disposable cartridge being configured according to a ninth embodiment and being hold in place without a clamp;

FIG. 13 a section view of one disposable cartridge before reaching its accommodation site, the disposable cartridge being configured according to a tenth embodiment and to be hold at the cartridge accommodation site with or without a clamp;

FIG. 14 a section view of one disposable cartridge before reaching its accommodation site, the disposable cartridge being configured according to an eleventh embodiment and to be hold in place at the cartridge accommodation site with or without a clamp;

FIG. 15 a partial section view of one disposable cartridge in its accommodation site, the disposable cartridge being configured according to a twelfth embodiment, centered in the cartridge accommodation site by a frame and pressed on a spacer of the PCB with a screwed plate;

FIG. 16 a partial section view of one disposable cartridge in its accommodation site, the disposable cartridge configured according to the twelfth embodiment being centered in the cartridge accommodation site and pressed on a spacer by a screwed frame profile;

FIG. 17 a partial section view of one disposable cartridge in its accommodation site, the disposable cartridge being configured according to the twelfth embodiment, centered in the cartridge accommodation site by a screwed frame and pressed on a spacer of the PCB with a pressing plate.

DETAILED DESCRIPTION OF THE PRESENT INVENTION

The FIG. 1 shows an overview over an exemplary digital microfluidics system 1 that is equipped with a central control unit 14 and a base unit 7, with four cartridge accommodation sites 8 that each comprise an electrode array 9, and a cover plate 12. The digital microfluidics system 1 is configured for manipulating samples in liquid droplets 23 within disposable cartridges 2 that contain a bottom layer 3, a top layer 4, and eventually a spacer 5 that defines a gap 6 between the bottom and top layers 3,4. Accordingly, the samples in liquid droplets 23 are manipulated in the gap 6 of the disposable cartridge 2.

A typical digital microfluidics system 1 comprises a base unit 7 with at least one cartridge accommodation site 8 that is configured for taking up a disposable cartridge 2. The digital microfluidics system 1 can be a stand alone and immobile unit, on which a number of operators is working with cartridges 2 that they bring along. The digital microfluidics system 1 thus may comprise a number of cartridge accommodation sites 8 and a number of electrode arrays 9, so that a number of cartridges 2 can be worked on simultaneously and/or parallel. The number of cartridge accommodation sites 8, electrode arrays 9, and cartridges 2 may be 1 or any number between e.g. 1 and 100 or even more; this number e.g. being limited by the working capacity of the central control unit 14.

It may be preferred to integrate the digital microfluidics system 1 into a liquid handling workstation or into a Freedom EVO® robotic workstation, so that a pipetting robot can be utilized to transfer liquid portions and/or sample containing liquids to and from the cartridges 2.

Alternatively, the system 1 can be can be configured as a hand held unit which only comprises and is able to work with a low number, e.g. a single disposable cartridge 2. Every person of skill will understand that intermediate solutions that are situated in-between the two extremes just mentioned will also operate and work.

A typical digital microfluidics system 1 also comprises at least one electrode array 9 that substantially extends in a first plane and that comprises a number of individual electrodes 10. Such an electrode array 9 is located at each one of said cartridge accommodation sites 8 of the base unit 7. Preferably each electrode array 9 is supported by a bottom substrate 11, which bottom substrate 11 is fixed to the base unit 7. It is noted that the expressions "electrode array", "electrode layout", and "printed circuit board (PCB)" are utilized herein as synonyms.

A typical digital microfluidics system 1 also comprises at least one cover plate 12 with a top substrate 13. In each case, at least one cover plate 12 is located at said cartridge accommodation sites 8. The top substrate 13 of the cover plate 12 and the bottom substrate 11 with the electrode array 9 or PCB define a space or cartridge accommodation site 8 respectively. In a first variant (see the two cartridge accommodation sites 8 in the middle of the base unit 7), the cartridge accommodation sites 8 are configured for receiving a slidingly inserted disposable cartridge 2 that is movable in a direction substantially parallel with respect to the electrode array 9 of the respective cartridge accommodating site 8. Such front- or top-loading can be supported by a drawing-in automatism that, following a partial insertion of a disposable cartridge 2, transports the cartridge 2 to its final destination within the cartridge accommodation site 8, where the cartridge 2 is precisely seated. Preferably, these cartridge accommodation sites 8 do not comprise a movable cover plate 12. After carrying out all intended manipulations to the samples in liquid droplets, the used cartridges 2 can be ejected by the drawing-in automatism and transported to an analysis station or discarded.

In a second variant (see the two cartridge accommodation sites 8 on the right and left of the base unit 7), the cartridge accommodation sites 8 comprise a cover plate 12 that is configured to be movable with respect to the electrode array 9 of the respective cartridge accommodating site 8. The cover plate 12 preferably is configured to be movable about one or more hinges 16 and/or in a direction that is substantially normal to the electrode array 9.

A typical digital microfluidics system 1 also comprises a central control unit 14 for controlling the selection of the individual electrodes 10 of said at least one electrode array 9 and for providing these electrodes 10 with individual voltage pulses for manipulating liquid droplets within said cartridges 2 by electrowetting. As partly indicated in FIG. 1, every single individual electrode 10 is operatively connected to the central control unit 14 and therefore can be independently addressed by this central control unit 14, which also comprises the appropriate sources for creating and providing the necessary electrical potentials in a way known in the art.

The at least one cover plate 12 further comprises an electrically conductive material 15 that extends in a second plane and substantially parallel to the electrode array 9 of the cartridge accommodation site 8 the at least one cover plate 12 is assigned to. This electrically conductive material 15 of the cover plate 12 preferably is configured to be connected to a source of an electrical ground potential. This conductive material 15 contributes to the electrowetting movements of the liquid droplets manipulated in the digital microfluidics system 1.

The applicants surprisingly found that the conductive material 15 also contributes to the electrowetting movements of the liquid droplets manipulated in the digital microfluidics system 1, if there is no connection between the conductive material 15 of the cover plate 12 and any source of a certain electrical (e.g. ground) potential. Thus, the cover plate 12 can be configured to be movable in any arbitrary direction and no electrical contacts have to be taken in into consideration when selecting a particularly preferred movement of the cover plate 12. Thus, the cover plate 12 may be configured to be also movable in a direction substantially parallel to the electrode array 9 and for carrying out a linear, circular or any arbitrary movement with respect to the respective electrode array 9 of the base unit 7.

The FIG. 2 shows a section view of one exemplary cartridge accommodation site 8 with a disposable cartridge 2 according to a first embodiment accommodated therein. The cover plate 12 is mechanically connected with the base unit 7 of the digital microfluidics system 1 via a hinge 16; thus, the cover plate 12 can swing open and a disposable cartridge 2 can be placed on the cartridge accommodation site 8 via top-entry loading (see FIG. 1). The electrically conductive material 15 of the cover plate 12 is configured as a thin metal plate or metal foil that is attached to the top substrate 13.

Alternatively, the electrically conductive material 15 of the cover plate 12 is configured as a metal layer that is deposited onto the top substrate 13. Such deposition of the conductive material 15 may be carried out by chemical or physical vapor deposition techniques as they are known per se.

The cover plate 12 is configured to apply a force to a disposable cartridge 2 that is accommodated at the cartridge accommodation site 8 of the base unit 7. This force urges the disposable cartridge 2 against the electrode array 9 in order to position the bottom layer 3 of the cartridge as close as possible to the surface of the electrode array 9. This force also urges the disposable cartridge 2 into the perfect position on the electrode array 9 with respect to a piercing facility 18 of the cover plate 12. This piercing facility 18 is configured for introducing sample droplets into the gap 6 of the cartridge 2. The piercing facility 18 is configured as a through hole 19 that leads across the entire cover plate 12 and that enables a piercing pipette tip 20 to be pushed through and pierce the top layer 4 of the cartridge 2. The piercing pipette tip 20 may be a part of a handheld pipette (not shown) or of a pipetting robot (not shown).

In this case, the electrode array 9 is covered by a dielectric layer 24. The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

The disposable cartridge 2 comprises a bottom layer 3, a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17 that is exposed to the gap 6 of the cartridge 2. The bottom layer 3 and the top layer 4 of the cartridge 2 are entirely hydrophobic films or at least comprise a hydrophobic surface that is exposed to the gap 6 of the cartridge 2. It is clear from this FIG. 2, that the cartridge 2 does not have a conductive layer. The spacer 5 of the cartridge 2 here at least partially is configured as a body that includes compartments 21 for reagents needed in an assay that is applied to the sample droplets in the gap 6.

The FIG. 3 shows a section view of one exemplary cartridge accommodation site 8 with a disposable cartridge 2 according to a second embodiment accommodated therein. Different to the previous embodiment, the cover plate 12 is mechanically connected with the base unit 7 of the digital microfluidics system 1 and immovably fixed therewith. The electrically conductive material 15 of the cover plate 12 is configured as a thick metal plate that is attached to the top substrate 13. Here, the cover plate 12 is not configured to apply a force to the disposable cartridge 2 that is accommodated at the cartridge accommodation site 8 of the base unit 7; thus, the cover plate 12 stays in place and a disposable cartridge 2 can be placed on the cartridge accommodation site 8 via front-entry loading. Such front-entry loading usually includes a movement of the disposable cartridge 2 in a direction that is parallel to the electrode array 9 (see FIG. 1). In order to enable proper drawing-in of the disposable cartridge 2 and to neatly position the cartridge at the accommodation site 8, the base unit 7 preferably is equipped with insertion guides 25. These insertion guides 25 preferably are from a self-lubricating plastic material, such as tetrafluorethylene and preferably leave a space between them that is just sufficient for slidingly inserting the disposable cartridge 2. Alternatively the electrically conductive material 15 of the cover plate 12 is configured as a metal plate, a metal foil, or a metal layer that is sandwiched between materials of the top substrate 13 (see FIG. 8A).

The disposable cartridge 2 of FIG. 3 comprises a bottom layer 3, a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17 that is exposed to the gap 6 of the cartridge 2. The bottom layer 3 and the top layer 4 of the cartridge 2 are entirely hydrophobic films or at least comprise a hydrophobic surface that is exposed to the gap 6 of the cartridge 2. As a difference to the one depicted in FIG. 2, this cartridge 2 has dielectric layer 24 that is attached to or forms a part of the bottom layer 3. Thus, the bottom layer 3 is covered by a dielectric layer 24 or the bottom layer 3 itself is made from a dielectric material. In consequence, the electrode array 9 does not need to have such a dielectric layer 24. The spacer 5 of the cartridge 2 here at least partially is configured as a body that includes compartments 21 for reagents needed in an assay that is applied to the sample droplets in the gap 6. In this case, the electrode array 9 is covered by a dielectric layer 24.

The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

The cover plate 12 also includes a piercing facility 18 that is configured for introducing sample droplets into the gap 6 of the cartridge 2. The piercing facility 18 is configured as a through hole 19 that leads across the entire cover plate 12 and that enables a piercing pipette tip 20 to be pushed through and pierce the top layer 4 of the cartridge 2. The piercing pipette tip 20 may be a part of a handheld pipette (not shown) or of a pipetting robot (not shown). The cover plate 12 here comprises additional piercing facilities 22 for a piercing pipette tip 20 to be pushed through a through hole 19 that penetrates the cover plate 12, to pierce the top layer 4 of the cartridge 2 and to withdraw reagent portions from the compartments 21 and for introducing said reagent portions into the gap 6 of the cartridge 2. Here, the compartment 21 is configured as a cutout in the body of the spacer 5, the cutout being closed by the bottom layer 3 and top layer 4.

The FIG. 4 shows section views of one exemplary cartridge accommodation site 8 with a disposable cartridge 2 according to a third embodiment accommodated therein. The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

The cover plate 12 is mechanically connected with the base unit 7 of the digital microfluidics system 1 via a hinge 16; thus, the cover plate 12 can swing open and a disposable cartridge 2 can be placed on the cartridge accommodation site 8 via top-entry loading (see FIG. 1). Here, the electrically conductive material 15 of the cover plate 12 is made of metallic conductive material and comprises both the top substrate 13 and the electrically conductive material 15 as a single integrated part. Alternatively, the electrically conductive material 15 of the cover plate 12 is configured as compound, such as titanium indium oxide (TIO) or a plastic material with electrically conductive filler materials that is attached or integrated into the top substrate 13 (not shown). In both cases, it may be preferred that the electrically conductive material 15 is covered by a plastic layer (not shown); the material of this plastic layer preferably being selected from a group comprising polypropylene (PP) and polyamide (PA). Automatic opening and closing of the cover plate 12 may be achieved by a closing means 30.

The cover plate 12 also includes a piercing facility 18 that is configured for introducing sample droplets into the gap 6 of the cartridge 2. The piercing facility 18 is configured as a through hole 19 that leads across the entire cover plate 12 and that enables a piercing pipette tip 20 to be pushed through and pierce the top layer 4 of the cartridge 2 (see FIG. 4B). The piercing pipette tip 20 may be a part of a handheld pipette (not shown) or of a pipetting robot (not shown). The cover plate 12 here comprises additional piercing facilities 22 for a piercing pipette tip 20 to be pushed through a through hole 19 that penetrates the cover plate 12, to pierce the top layer 4 of the cartridge 2 and to withdraw e.g. silicon oil from the gap 6 of the cartridge 2 (see FIG. 4B).

FIG. 4A shows the cushion-like cartridge 2 as laid into a cartridge accommodation site 8 of a base unit 7 of digital microfluidics system 1 a with a partly closed cover plate 12. This disposable cartridge 2 comprises a bottom layer 3 and a top layer 4, but no spacer that would define a gap 6 between the bottom and top layers 3,4 for manipulating samples in liquid droplets 23 in this gap 6. The bottom layer 3 and the top layer 4 comprise a hydrophobic surface 17',17" that is exposed to the gap 6 of the cartridge 2. The bottom layer 3 and the top layer 4 of the cartridge 2 are entirely hydrophobic films or at least comprise a hydrophobic surface that is exposed to the gap 6 of the cartridge 2. Like the one depicted in FIG. 2, this cartridge 2 has no dielectric layer attached to or forms a part of the bottom layer 3. In consequence, the electrode array 9 does need to have such a dielectric layer 24. This cartridge 2 without spacer is configured as a sack or pillow that preferably is filled with silicon oil, other oils or another chemically substantially inert material that is not miscible with water, such as hexadecane.

FIG. 4B shows the cushion-like cartridge 2 as pressed into operation shape inside the cartridge accommodation site 8 by the entirely closed cover plate 12. As long as the cover plate 12 at least partially is open (see FIG. 4A), the cushion-like or sack-like cartridge 2 may take a shape that is mainly due to the forces that the preferred oil filling is exerting to the membrane bag or sack of the cartridge 2. Handling (inserting into and taking out from the accommodation site 8) the cartridge 2 preferably is performed with a robotized suction device (not shown). When pressed into operation shape however (see FIG. 4B), the cushion-like or sack-like cartridge 2 is urged into a shape that conforms to the inner space of the cartridge accommodation site 8 of the base unit 7. Thus, without any need for providing a spacer, the top layer 4 is orientated substantially parallel and in a defined distance to the bottom layer 3 and to the electrode array 9 below the latter.

In order to avoid leakage or spilling of oil during or after piercing the pillow-like cartridge 2, the top layer 4 of the cartridge 2 may be configured as a self-sealing pierceable membrane. Alternatively or in combination with a self-sealing pierceable top layer 4, the cover plate 12 may be equipped with a self-sealing pierceable membrane at least in the region of the piercing facilities 18,22. Such a self-sealing pierceable membrane at least in the region of the piercing facilities 18,22 (not shown) preferably is placed onto the surface of the cover plate 12 that is contacting the cartridge 2.

The FIG. 5 shows a section view of one exemplary cartridge accommodation site 8 with a disposable cartridge 2 according to a fourth embodiment accommodated therein. The cover plate 12 is mechanically connected with the base unit 7 of the digital microfluidics system 1 via a hinge 16; thus, the cover plate 12 can swing open and a disposable cartridge 2 can be placed on the cartridge accommodation site 8 via top-entry loading (see FIG. 1). Here, the electrically conductive material 15 of the cover plate 12 is made of metallic conductive material and comprises both the top substrate 13 and the electrically conductive material 15 as a single integrated part. Alternatively, the electrically conductive material 15 of the cover plate 12 is configured as compound, such as titanium indium oxide (TIO) or a plastic material with electrically conductive filler materials that is attached or integrated into the top substrate 13 (not shown). In both cases, it may be preferred that the electrically conductive material 15 is covered by a plastic layer (not shown); the material of this plastic layer preferably being selected from a group comprising polypropylene (PP) and polyamide (PA).

Also here, the cover plate 12 is configured to apply a force to a disposable cartridge 2 that is accommodated at the cartridge accommodation site 8 of the base unit 7. This force urges the disposable cartridge 2 against the electrode array 9 in order to position the bottom layer 3 of the cartridge as close as possible to the surface of the electrode array 9. This force also urges the disposable cartridge 2 into a defined position on the electrode array 9. In addition, a piercing facility 18 is provided: The disposable cartridge 2 according to this third embodiment comprises a piercing pin 27 that is located in the gap 6 of the cartridge 2 and that is configured for piercing the top layer 4 when the top layer 4 is displaced in a direction against the bottom layer 3. Preferably, the piercing pin 27 is attached to a pin plate 28, which pin plate 28 is connecting the piercing pin 27 with a part of the spacer 5 of the disposable cartridge 2. The cover plate 12 further comprises a through hole 19 that leads across the entire cover plate 12 and that is located in register with the piercing pin 27 of a properly positioned disposable cartridge 2 seated at the cartridge accommodation site 8. The cover plate 12 further comprises a displacement portion 29, which protrudes from the cover plate 12 for displacing the top layer 4 in a direction against the bottom layer 3. This displacement portion 29 is configured to cooperate with the piercing pin 27 when piercing the top layer 4. Thus, by utilization of this piercing facility 18, sample droplets and/or reagent portions may be introduced into the gap 6 of the cartridge 2. A portion of the through hole 19 preferably is widened such that a disposable pipette tip 26 may be used for pipetting sample droplets and/or reagent portions to the gap 6 of the disposable cartridge 2. The disposable pipette tip 26 may be a part of a handheld pipette (not shown) or of a pipetting robot (not shown).

In this case, the electrode array 9 is covered by a dielectric layer 24. The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

Like in the already introduced first and second embodiments, the disposable cartridge 2 comprises a bottom layer 3, a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17 that is exposed to the gap 6 of the cartridge 2. The $1^{st}$ hydrophobic surface 17' is located on the inside of the bottom layer 3, and the $2^{nd}$ hydrophobic surface 17" is located on the inside of the top layer 4. The bottom layer 3 and the top layer 4 of the cartridge 2 are entirely hydrophobic films or at least comprise a hydrophobic surface that is exposed to the gap 6 of the cartridge 2. It is clear from this FIG. 2, that the cartridge 2 does not have a conductive layer. The spacer 5 of the cartridge 2 here does not deed to be configured as a body that includes compartments 21 for reagents needed in an assay that is applied to the sample droplets in the gap 6, because these reagents could be added to the gap 6 by conventional pipetting with a handheld pipette or with a pipetting robot (see above).

The FIG. 6 shows a section view of one exemplary cartridge accommodation site 8 with a disposable cartridge 2 according to a fifth embodiment accommodated therein. Similar to the previous embodiment, the cover plate 12 is mechanically connected with the base unit 7 of the digital microfluidics system 1 by a hinge 16. In order to enable proper top-loading of the disposable cartridge 2 and to neatly position the cartridge at the accommodation site 8, the base unit 7 preferably is equipped with insertion guides 25. These insertion guides 25 preferably are from a self-lubricating plastic material, such as tetrafluorethylene (PTFE) and preferably leave a space between them that is just sufficient for slidingly inserting the disposable cartridge 2. Also similar to the previous embodiment and as a first alternative solution, the electrically conductive material 15 of the cover plate 12 is made of metallic conductive material and comprises both the top substrate 13 and the electrically conductive material 15 as a single integrated part. Alternatively, the electrically conductive material 15 of the cover plate 12 is configured as compound, such as titanium indium oxide (TIO) or a plastic material with electrically conductive filler materials that is attached or integrated into the top substrate 13 (not shown). In both cases, it may be preferred that the electrically conductive material 15 is covered by a plastic layer (not shown); the material of this plastic layer preferably being selected from a group comprising polypropylene and polyamide.

Also here, the cover plate 12 is configured to apply a force to a disposable cartridge 2 that is accommodated at the cartridge accommodation site 8 of the base unit 7. This force urges the disposable cartridge 2 against the electrode array 9 in order to position the bottom layer 3 of the cartridge as close as possible to the surface of the electrode array 9. This force also urges the disposable cartridge 2 into a defined position on the electrode array 9. In addition, a piercing facility 18 is provided: The disposable cartridge 2 according to this third embodiment comprises a piercing pin 27 that is located in the gap 6 of the cartridge 2 and that is configured for piercing the top layer 4 when the top layer 4 is displaced in a direction against the bottom layer 3. Preferably, the piercing pin 27 is attached to a pin plate 28, which pin plate 28 is connecting the piercing pin 27 with a part of the spacer 5 of the disposable cartridge 2. The cover plate 12 further comprises a through hole 19 that leads across the entire cover plate 12 and that is located in register with the piercing pin 27 of a properly positioned disposable cartridge 2 seated at the cartridge accommodation site 8. The cover plate 12 further comprises a displacement portion 29, which protrudes from the cover plate 12 for displacing the top layer 4 in a direction against the bottom layer 3. This displacement portion 29 is configured to cooperate with the piercing pin 27 when piercing the top layer 4. Thus, by utilization of this piercing facility 18, sample droplets and/or reagent portions may be introduced into the gap 6 of the cartridge 2. A portion of the through hole 19 preferably is widened such that a disposable pipette tip 26 may be used for pipetting sample droplets and/or reagent portions to the gap 6 of the disposable cartridge 2. The disposable pipette tip 26 may be a part of a handheld pipette (not shown) or of a pipetting robot (not shown).

In this case, the electrode array 9 is covered by a dielectric layer 24. The electrode array 9 is fixed to a bottom substrate 11 and every individual electrode 10 is electrically and operationally connected with the central control unit 14 (only three connections of the ten electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

Like in the already introduced first, second, and fourth embodiment, the disposable cartridge 2 comprises a bottom layer 3, a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17 that is exposed to the gap 6 of the cartridge 2. The $1^{st}$ hydrophobic surface 17' is located on the inside of the bottom layer 3, and the $2^{nd}$ hydrophobic surface 17" is located on the inside of the top layer 4. The bottom layer 3 and the top layer 4 of the cartridge 2 are entirely hydrophobic films or at least comprise a hydrophobic surface that is exposed to the gap 6 of the cartridge 2. It is clear from this FIG. 2, that the cartridge 2 does not have a conductive layer. The spacer 5 of the cartridge 2 here does not deed to be configured as a body that includes compartments 21 for reagents needed in an assay that is applied to the sample droplets in the gap 6, because these reagents could be added to the gap 6 by conventional pipetting with a handheld pipette or with a pipetting robot (see above).

It is noted that the piercing pin 27 of the fourth embodiment (see FIG. 5) of the disposable cartridge 2 is placed with its back on the $1^{st}$ hydrophobic surface of the bottom layer 3. Thus, the bottom substrate 11 and the electrode array 9 provide stability to the piercing pin 27 when the top layer 4 is displaced by the displacement portion 29 of the cover plate 12. In consequence, the pin plate 28 can be very thin.

Alternatively, the pin plate 28 is omitted and the piercing pin 27 is glued to the $1^{st}$ hydrophobic surface of the bottom layer 3. Only gluing such a small piercing pin 27 to the inner surface of the bottom layer 3 has the advantage that more of the individual electrodes 10 can be used for electrowetting. Another advantage is that the position of the piercing pin 27 (and also of the through hole 19 in the cover plate 12 of course) can be arbitrarily chosen in any distance to the spacer 5. However, exact positioning of the piercing pin 27 may be somewhat cumbersome during mass production of the disposable cartridges 2.

In contrast, the piercing pin 27 of the fifth embodiment of the disposable cartridge 2 (see FIG. 6) is placed much closer to the spacer 5 with which it is connected by a self-supporting pin plate 28. Thus, the spacer 6 provides stability to the piercing pin 27 when the top layer 4 is displaced by the displacement portion 29 of the cover plate 12. Advantageously, the electrode array 9 is not involved or affected by the piercing process and all of the individual electrodes 10 can be used for electrowetting. It is preferred to add a so-called weather groove to the lower part of the piecing pin 27 (see FIG. 6) if draining the pipetted liquid down to the $1^{st}$ hydrophobic surface 17' along the self-supporting pin plate 28 should be avoided. If such draining down however is preferred, adding of such a weather groove can be omitted.

The FIG. 7 shows an overview over a digital microfluidics system 1 that is equipped with a central control unit 14 and a base unit 7, with twelve cartridge accommodation sites 8 that each comprise an electrode array 9 and a fixed cover plate 12. This base unit 7 is particularly suited for taking up cartridges 2 according to a sixth embodiment and loading these cartridges into substantially vertical cartridge accommodation sites 8 with a substantially vertical electrode array 9 and cover plate 12 (see FIG. 8). Such loading preferably is carried out by a robotized gripping device of a liquid handling workstation (not shown).

The FIG. 8 shows section views of one exemplary cartridge accommodation site 8 of a base unit 7 of digital microfluidics system 1 with a disposable cartridge 2 according to a sixth embodiment accommodated therein. It is immediately clear from the FIG. 8A, that a top-entry cartridge 2 is inserted into a substantially vertical cartridge accommodation site 8 with a substantially vertical electrode array 9 and cover plate 12. This disposable cartridge 2 comprises a bottom layer 3 and a top layer 4, and a spacer 5 that defines a gap 6 between the bottom and top layers 3,4 for manipulating samples in liquid droplets 23 in this gap 6. The bottom layer 3 and the top layer 4 comprise a hydrophobic surface 17',17" that is exposed to the gap 6 of the cartridge 2. The bottom layer 3 and the top layer 4 of the cartridge 2 are entirely hydrophobic films or at least comprise a hydrophobic surface that is exposed to the gap 6 of the cartridge 2. Like the one depicted in FIG. 2, this cartridge 2 has no dielectric layer attached to or forms a part of the bottom layer 3. In consequence, the electrode array 9 does need to have such a dielectric layer 24. This cartridge 2 preferably is filled with silicon oil.

The electrode array 9 is fixed to a bottom substrate 11 and every individual electrode 10 is electrically and operationally connected with the central control unit 14 (only four connections of the fourteen electrodes 10 are drawn here). The digital microfluidics system 1 is configured for manipulating samples in liquid droplets 23 within disposable cartridges 2 that contain a gap 6. Accordingly, the samples in liquid droplets 23 are manipulated in the gap 6 of the disposable cartridge 2.

The cover plate 12 is mechanically connected with or entirely integrated into the base unit 7 of the digital microfluidics system 1 and is not movable. Thus, a disposable cartridge 2 can be inserted into the cartridge accommodation site 8 via top-entry loading (see FIG. 7). Here, the electrically conductive material 15 of the cover plate 12 is made of metallic conductive material and is sandwiched between material of the top substrate 13. Alternatively, the electrically conductive material 15 of the cover plate 12 may be covered by a plastic layer instead or additional to the material of the top substrate 13 (not shown).

The spacer 5 also includes a piercing facility 18 that is configured for introducing sample droplets into the gap 6 of the cartridge 2. The piercing facility 18 is configured as an enlarged portion of the spacer 5. This enlarged spacer portion preferably is equipped with a pierceable, self-sealing membrane 31 that enables a piercing pipette tip 20 to be pushed through. The piercing pipette tip 20 may be a part of a handheld pipette (not shown) or of a pipetting robot (not shown). Automated delivery of liquids to or withdrawal of liquids from the gap 6 of the cartridge 2 is simplified by the relatively large piercing area provided by this enlarged spacer portion of the cartridge 2. Assuming a gap width of about 1-3 mm, the width of this piercing area preferably is about 5-10 mm and therefore has about the size of a well of 96-well microplate, which easily can be reached by an automated pipettor of a liquid handling system or of a liquid handling workstation. The same time as providing space for compartments 21 (see also FIG. 8B), the enlarged spacer portion of the cartridge 2 also provides gripping surfaces for being gripped by an automated robot gripper (not shown) that is preferably utilized for handling the cartridges outside of the digital microfluidics system 1 and for inserting and withdrawal of the cartridges 2 from their accommodation sites 8. In addition, the enlarged spacer portion of the cartridge 2 provides an abutting surface that abuts the surface of the base unit 7 when the cartridge 2 is correctly accommodated in the accommodation site 8.

It is preferred that the electrode array 9 extends to the foremost position with respect to the surface of the base unit 7 in order to be able to move liquid droplets 23 from a compartment 21 to a distinct position on the printed circuit board (PCB) or electrode array 9. Also moving liquid droplets 23 in the opposite direction from a reaction site on the electrode array 9 to a compartment 21 is greatly preferred, especially in the case if a reaction product shall be analyzed outside of the digital microfluidics system 1 and also outside of the cartridge 2.

FIG. 8B shows the top-entry cartridge 2 of FIG. 8A as viewed from the section plane B indicated in FIG. 8A. The section runs through the gap 6 and between the bottom layer 3 and the top layer 4 of the self-containing, disposable cartridge 2. The section also crosses the spacer 5, of which a U-shaped part is located between the bottom and top layers 3,4 and an enlarged spacer portion is provided around the U-shaped part and the bottom and top layers 3,4. Preferably, the U-shaped part of the spacer 5 is of plastic material (preferably injection molded) and glued or fused to the bottom and top layers 3,4. It is preferred that the enlarged spacer portion also is produced by injection molding; this enables the provision of separating bars 32 that on the one hand create the compartments 21 below the pierceable membrane 31, and that on the other hand stabilize the pierceable membrane 31. Such stabilization preferably is provided by back-injection molding the separating bars 32 and the enlarged spacer portion to the pierceable membrane 31. Preferably, the enlarged spacer portion then is imposed on the U-shaped part of the spacer 5 with the bottom and top layers 3,4.

As already pointed out, the spacer 5 also includes a piercing facility 18 that is configured as an enlarged portion of the spacer 5. This enlarged spacer portion preferably is equipped with a pierceable self-sealing membrane 31 that enables a piercing pipette tip 20 to be pushed through. The piercing pipette tip 20 may be a part of a handheld pipette (not shown) or of a pipetting robot (not shown). The spacer 2 here comprises additional piercing facilities 22 for a piercing pipette tip 20 to be pushed through the self-sealing membrane 31 and to withdraw e.g. silicon oil from the gap 6 of the cartridge 2. In the cartridge 2 of this FIG. 8B, a liquid droplet 23 (e.g. a sample) was introduced by the piercing pipette tip 20 at the piercing facility 18 and then moved on the hydrophobic surface 17' of the bottom layer 3 to the actual position. Simultaneously with introducing the liquid droplet 23 into the compartment 21 and into the gap 6, a similar amount of silicon oil (or any other chemically inert liquid that will not mix with the liquid droplet 23) is withdrawn from the respective compartment 21 at the additional piercing facility 22. Alternative to such simultaneous balancing of liquids in the gap 6, removing of the expected quantity of oil or inert liquid can be carried out shortly before or after the insertion of the liquid droplet 23. The compartments 21 also may serve as reservoirs for storing more liquid than necessary for producing a movable liquid droplet 23 from this liquid; in consequence, a number of such droplets 23 may be produced from a single liquid volume once introduced into at least one of the compartments 21. It is advisable however, to set aside one compartment 21, for withdrawal of oil or inert liquid, and to set aside another compartment 21 for withdrawal of reagent products.

According to an alternative and very simple embodiment (not shown), a disposable cartridge 2 that comprises a bottom layer 3 and top layer 4 with hydrophobic surfaces 17',17" that in each case are directed to the gap 6, can be mounted on a PCB for electrowetting. Instead of utilizing a cover plate 12 that is equipped with an electrically conductive material 15, an electrically conductive film (e.g. an aluminum foil) can be attached to the outer surface of the top layer 4. It turned out that such a conductive film enables electrowetting even when this conductive film in not grounded. Instead of attaching an un-grounded conductive film to the cartridge, the top layer 4 can have a thin film coating on its outer surface; the thin film coating can be of any metal and deposited by chemical or physical evaporation techniques. This thin conductive film on the outer surface of the top layer 4 can even by of conductive paint. It is thus proposed to provide an electrically conductive material 15 that extends in a second plane and substantially parallel to the electrode array 9, said electrically conductive material 15 being situated on the top layer 4 of the cartridge 2 and being not connected to a source of a distinct electrical potential during manipulating samples in liquid droplets 23.

A method for manipulating samples in liquid droplets 23 that adhere to a hydrophobic surface 17 is characterized that the method comprising the steps of providing a first hydrophobic surface 17' on a bottom layer 3 of a disposable cartridge 2. This bottom layer 3 is located substantially parallel above an electrode array 9 of a digital microfluidics system 1. Said electrode array 9 substantially extends in a first plane and comprises a number of individual electrodes 10 that are supported by a bottom substrate 11 of a base unit 7 of the digital microfluidics system 1. Said electrode array 9 is connected to a central control unit 14 of the digital microfluidics system 1 for controlling the selection of individual electrodes 10 of said electrode array 9 and for providing these electrodes 10 with individual voltage pulses for manipulating said liquid droplets 23 on said first hydrophobic surface 17' by electrowetting.

The method also comprises the step of providing a second hydrophobic surface 17" substantially parallel to and in a distance to said first hydrophobic surface 17'. In this way, a gap 6 between the first and second hydrophobic surfaces 17',17" is formed. Preferably, such a gap 6 is defined by a spacer 5, to which the a bottom layer 3 that comprises the first hydrophobic surface 17' and a top layer 4 that comprises the second hydrophobic surface 17" are attached.

The method further comprises providing a cover plate 12 with a top substrate 13. The cover plate 12 also comprises an electrically conductive material 15 that extends in a second plane and substantially parallel to the electrode array 9. It is especially preferred that the electrically conductive material 15 of the cover plate 12 is not connected to a source of a distinct electrical potential during manipulating samples in liquid droplets 23.

In all embodiments shown or discussed, it is preferred that the gap 6 of the disposable cartridge 2 is substantially filled with silicon oil. It is also always preferred that the bottom layer 3 and the top layer 4 of the cartridge 2 are entirely hydrophobic films or comprise a hydrophobic surface 17', 17" that is exposed to the gap 6 of the cartridge 2. Following electrowetting and manipulating at least one liquid droplet 23 with the gap 6 of a disposable cartridge 2, the result of the manipulation or of the assay can be evaluated while the disposable cartridge 2 still is at the cartridge accommodation site 8, i.e. utilizing an analysis system of the digital microfluidics system 1 or of a workstation, the digital microfluidics system 1 is integrated into. Alternately, the disposable cartridges 2 can be taken out of the base unit 7 of the digital microfluidics system 1 and analyzed elsewhere.

After analysis, the disposable cartridges 2 can be disposed and the electrode array 9 can be reused. Because the components of the digital microfluidics system 1 never come into contact with any samples or reagents when working with the first or second embodiment of the cartridge 2, such re-usage with other disposable cartridges 2 can be immediately and without any intermediate cleaning. Because the through hole 19 of the cover plate 12 of the digital microfluidics system 1 may come into contact with samples and reagents when working with the third or fourth embodiment of the cartridge 2, such re-usage with other disposable cartridges 2 can be carried out after some intermediate cleaning or after replacement of the cover plates 12.

It is an aim of the present invention to provide removable and disposable cartridges with working films that separate the liquid droplets 23 from the electrode array 9 during manipulation of the liquid droplets 23 by electrowetting. As shown in the eight different embodiments of the self-containing disposable cartridge 2 presented in the above specification, the removable and disposable films preferably are provided as a bottom layer 3 and a top layer 4 of a cartridge 2.

In a preferred embodiment, the bottom layer 3 of the cartridge 2 is attracted to the PCB by vacuum. Small evacuation holes in the PCB are connected to a vacuum pump for this purpose. Applying such vacuum attraction to the bottom layer 3 enables avoiding the use of any liquids or adhesives for better contacting the bottom layer 3 of the cartridge 2 to the surface of the electrode array 9.

In the attached FIGS. 9, 10, and 11, especially preferred embodiments of a disposable cartridge according to a seventh and eighth embodiment are shown. In each case, the disposable cartridge 2 comprises a body 47 with at least one compartment 21 that is configured to hold therein processing liquids, reagents or samples. At least one of said compartments 21 comprises a through hole 19 for delivering at least some of its content to a gap 6 below. The disposable cartridge 2 also comprises a bottom layer 3 with a first hydrophobic surface 17' that is impermeable to liquids and that is configured as a working film for manipulating samples in liquid droplets 23 thereon utilizing an electrode array 9 of a digital microfluidics system 1 when the bottom layer 3 of the disposable cartridge 2 is placed over said electrode array 9. The disposable cartridge 2 further comprises a top layer 4 with a second hydrophobic surface 17" that at least is permeable to ions and that is attached to a lower surface 48 of the body 47 of the disposable cartridge 2. Moreover, the disposable cartridge 2 comprises a gap 6 that is located between the first hydrophobic surface 17' of the bottom layer 3 and the second hydrophobic surface 17" of the top layer 4. The bottom layer 3 of the inventive cartridge 2 is configured as a flexible film that is sealingly attached to the top layer 4 along a circumference 40 of the flexible bottom layer 3. Thus, the disposable cartridge 2 is devoid of any spacer 5 that is located between the flexible bottom layer 3 and the top layer 4 for defining a particular distance between said first hydrophobic surface 17' and said second hydrophobic surface 17". The top layer 4 is configured to provide a seal between a lower end of at least one compartment 21 and the gap 6. In addition, the top layer 4 comprises loading sites 41 for transferring processing liquids, reagents or samples into the gap 6.

In FIG. 9, a section view of one disposable cartridge 2 before reaching its accommodation site 8 is presented. The flexible bottom layer 3 is seen as it is only attached to the top layer 4 around its circumference 40, the majority of the bottom layer 3 being loosely suspended from its circumference 40 and being not in contact with the top layer 4. Accordingly, before correctly placing the disposable cartridge 2 in or on the cartridge accommodation site 8, the gap 6 is enclosed but not defined in its width and parallel orientation. The body 47 of the disposable cartridge 2 here comprises an essentially flat lower surface 48 and is configured as a frame structure with a central opening 43 that penetrates the entire frame structure.

In FIG. 10, a section view of the disposable cartridge 2 of FIG. 9 is depicted after the disposable cartridge 2 reaching its cartridge accommodation site 8 on the electrode array of a digital microfluidics system 1. The disposable cartridge 2 is configured according to the seventh embodiment and is hold in place by a clamp 37. On one side, the clamp 37 preferably is attached to the substrate 11 of the base unit 7 of the digital microfluidics system 1 by a hinge 16. On the other side, the clamp 37 may be attached to the substrate 11 of the base unit 7 of the digital microfluidics system 1 by e.g. a clip, a snap-lock, or a screw (not shown).

In the seventh embodiment of FIGS. 9 and 10, the disposable cartridge 2 further comprises a plane rigid cover plate 12 that is attached to the lower surface 48 of the body 47 of the disposable cartridge 2. The top layer 4 is attached to said rigid cover plate 12, which rigid cover plate 12 comprises through holes 19 that are located at the loading sites 41 (here at the piercing site 41' and at the capillary orifice 41") of the top layer 4. The rigid cover plate 12 here provides for a straight attachment surface for the top layer 4 and also comprises the through hole 19. The cover plate may be manufactured from a rigid material like clear Mylar® (trademark of DuPont Teijin; a film from polyethylene terephthalate, PET). The rigid cover may be coated (preferably on the lower side) with an electrically conductive material 15, e.g. from titanium indium oxide (TIO) or from a plastic material with electrically conductive filler materials in order to achieve the function of the cover plate 12 as described before. As indicated with darker lines, the cover plate 12 is attached to the lower surface 48 of the body 47 of the disposable cartridge 2. This attachment may be achieved by the use of an adhesive tape or a glue strip that preferably is from a chemically inert material just like the Mylar. Depending on the material of the body 47 of the cartridge 2, also welding methods can be applied for attaching the cover plate 12 to the cartridge 2. As indicated with darker lines, the top layer 4 here is sealingly attached to the lower surface 48 of cover plate 12. This attachment of the top layer 4 can be carried out by using an adhesive tape or a glue strip, or by welding (e.g. by laser welding). The flexible bottom layer 3 is sealingly attached to the top layer 4 along the circumference 40 of the flexible bottom layer 3 by using an adhesive tape or a glue strip, or by applying a welding technique.

In FIG. 9, a pipetting orifice 41''' is depicted as well. Such pipetting orifices 41''' that are located in the central opening 43 of the disposable cartridge 2 and that are configured to be accessible by a pipette tip can thus be used for pipetting of processing liquids, reagents or samples directly into the gap 6. Of course, the pipetting orifice 41''' comprises an opening in the cover plate 12 (if present) and a through hole in the top layer 4. Such pipetting orifices 41''' can be used in addition to or instead of one or more piecing orifices 41', which in each case are located below a compartment 21.

This disposable cartridge 2 comprises at least one plunger 42 that in each case is configured to be movable within a compartment 21 manually or by an actuating element 38 (see FIG. 10) for pressing the content of the respective compartment 21 against a respective loading site 41 of the top layer 4. The plunger 42 comprises a piercing pin 27 that is configured for piercing the top layer 4 at the respective loading site 41 of the compartment 21. Thus, the plunger 42 is configured for pressing some of the content of the compartment 21 through the piercing site 41' of the top layer 4 and into the gap 6. Alternatively, the plunger 42 is configured for pressing some of the content of the compartment 21 through a capillary orifice 41'' of the top layer 4 and into the gap 6. This capillary orifice 41'' preferably is sized to exhibit capillary forces that prevent flowing though of aqueous liquids without a pressure being applied with the plunger 42 (see FIG. 11, left side). Thus, the loading sites 41 preferably are selected from a group comprising piercing sites 41', capillary orifices 41'', and pipetting orifices 41'''.

In FIG. 11, a section view of a disposable cartridge 2 after reaching its cartridge accommodation site 8 on the electrode array 9 of a digital microfluidics system 1 is shown. The disposable cartridge 2 is configured according to an eighth embodiment and is hold in place by a clamp 37.

In the FIG. 11, the plunger 42 is configured to sealing the compartment 21 against an upper surface 49 of the body 47 of the disposable cartridge 2. Preferably, this sealing is achieved with an O-ring seal 39 around the plunger 42. Alternatively, as shown in the FIGS. 9 and 10, to an upper surface 49 of the body 47 of the disposable cartridge 2 is sealingly applied an elastic layer 44 that is configured to seal at least one of the compartments 21 against said upper surface 49. Preferably, the plunger 42 is attached to the elastic layer 44 with its backside, so without applying any pressure to the outside of the elastic layer (manually or with an actuating element 38, see FIG. 10), the plunger 42 is held in place close to the upper surface 49 of the body 47 (see FIG. 9).

If however, the plunger 42 is pressed down (see FIG. 10 and FIG. 11, on the right), the piercing pin 27 penetrates the through hole 19 in the cover layer 12 or body 47 and pierces the top layer 4. Concurrently, a portion of the content of the compartment 21, be it a processing liquid, a reagent or a sample (in a solution or suspension), is pressed by the plunger into the gap 6. As a result, on the first hydrophobic surface 17' of the bottom layer 3, a droplet 23 is built up and can be manipulated in the gap between this first hydrophobic surface 17' of the bottom layer 3 and the second hydrophobic surface 17'' of the top layer 4. Manipulating the droplet 23 is effected by the electrode array 9 of the digital microfluidics system 1 the disposable cartridge 2 is accommodated on.

Alternatively, pressing down the plunger 42 shall force a portion of the contents of the compartment 21, be it a processing liquid, a reagent or a sample (in a solution or suspension), to be moved through the capillary orifice 41'' and into the gap 6 (see FIG. 11, left side, where the plunger 42 is ready to move). As a result, on the first hydrophobic surface 17' of the bottom layer 3, a droplet 23 will be built up and can be manipulated in the gap between this first hydrophobic surface 17' of the bottom layer 3 and the second hydrophobic surface 17'' of the top layer 4. Again, manipulating the droplet 23 will be effected by the electrode array 9 of the digital microfluidics system 1 the disposable cartridge 2 is accommodated on.

According to the eighth embodiment of FIG. 11, the body 47 of the disposable cartridge 2 is configured as a plate-like structure with an essentially flat lower surface 48, in each case the compartments 21 leading to said lower surface 48 with a through hole 19 at the piercing sites 41' or capillary orifices 41''.

In the seventh and eighth embodiment of the disposable cartridge 2 of the present invention, it is one preferred alternative that the flexible bottom layer 3 is configured as a monolayer or single layer, respectively of a hydrophobic material. According to a second preferred alternative, the flexible bottom layer 3 is configured as a monolayer or single layer, respectively of electrically non-conductive material, the upper surface 17 of the flexible bottom layer 3 being treated to be hydrophobic. According to a third preferred alternative, the flexible bottom layer 3 is configured as a laminate comprising a lower layer and a hydrophobic upper layer, the lower layer being electrically conductive or non-conductive. According to another preferred embodiment of the disposable cartridge 2 of the present invention, a dielectric layer 24 is laminated onto the lower surface of the bottom layer 3 (see e.g. FIG. 11).

According to one variant of the seventh and eighth embodiment of the disposable cartridge of the present invention, the disposable cartridge 2 further comprises a gasket 36 that is attached to a lower surface and along a circumference 40 of the flexible bottom layer 3. The gasket 36 thus defining a particular distance between said first hydrophobic surface 17' and said second hydrophobic surface 17'', when the disposable cartridge 2 is placed over an electrode array 9 of a digital microfluidics system 1. This is the case, if said digital microfluidics system 1 is equipped with suction holes 35 in the electrode array 9, and if the flexible bottom layer 3 is aspirated by said suction holes 35.

FIG. 12 shows a section view of a disposable cartridge 2 after reaching its accommodation site 8, the disposable cartridge 2 being configured according to a ninth embodiment and being hold in place without a clamp. Actually, two different variants of the ninth embodiment are shown:
- on the left side, the body 47 is configured as plate structure;
- on the right side, the body 47 is configured as frame structure;
- with the lower surface 48 of the body 47 of the disposable cartridge 2 in both cases being essentially flat. Thus, the disposable cartridge 2 configured according to the ninth embodiment comprises a body 47 with a lower surface 48, an upper surface 49, and at least one through hole 19. The at least one through hole 19 is designed as a pipetting orifice 41''' that is configured to be accessible by a pipette tip 26. The through hole 19 and thus allows pipetting of processing liquids, reagents or samples into the gap 6.

In addition to the body 47, the disposable cartridge 2 comprises a bottom layer 3 with a first hydrophobic surface 17' that is impermeable to liquids and that is configured as a working film for manipulating samples in liquid droplets 23 thereon. Such manipulating is performed utilizing an electrode array 9 of a digital microfluidics system 1 when the bottom layer 3 of the disposable cartridge 2 is placed over said electrode array 9. Preferably, the flexible bottom layer 3 is sealingly attached to an electrically conductive material 15 along a circumference 40 of the flexible bottom layer 3 by an adhesive tape or a glue strip, or alternatively by welding.

The disposable cartridge 2 further comprises an electrically conductive material 15 attached to the lower surface 48 of the body 47. The electrically conductive material 15 is at least permeable to ions and is configured to provide the lower surface 48 of the body 47 with a second hydrophobic surface 17''. The bottom layer 3 is configured as a flexible film that is sealingly attached to the electrically conductive material 15 of the disposable cartridge 2 along a circumference 40 of the flexible bottom layer 3, the disposable cartridge 2 thus being devoid of a spacer 5 (cv. FIGS. 2, 6, and 8-10) that is located between the flexible bottom layer 3 and the electrically conductive material 15 for defining a particular distance between said first hydrophobic surface 17' and said second hydrophobic surface 17''.

The disposable cartridge 2 further comprises a gap 6 that is located between the first hydrophobic surface 17' of the bottom layer 3 and the second hydrophobic surface 17'' of the electrically conductive material 15. The at least one through hole 19 of the body 47 is configured as a loading site 41 for transferring processing liquids, reagents or samples into the gap 6.

The disposable cartridge 2 further comprises something like a compartment 21, which is configured as one or more container-like depressions in the body 47 located around one or more loading sites 41. However, these compartments 21 are not meant to store liquids over a long period of time or even during shipping, they are merely configured to allow a pipette tip 26 (disposable or not) to reach near the pipetting orifices 41''' located at the loading sites 41. Preferably, these "compartments 21" comprise a central depression around the loading sites 41, which central depression allows some liquid to be deposited temporarily prior to the transfer of the liquid into the gap 6.

The FIG. 13 shows a section view of one disposable cartridge 2 before reaching its accommodation site 8 of the digital microfluidics system 1. The disposable cartridge depicted here is configured according to a tenth embodiment and to be hold at the cartridge accommodation site with or without a clamp. Despite some similarities when compared with the disposable cartridge according to the seventh embodiment (see above and FIG. 9), this tenth embodiment is characterized in that it is devoid of compartments 21. In consequence, this tenth embodiment of a disposable cartridge 2 according to the present invention comprises at least one through hole 19 that is configured as a loading site 41 for transferring processing liquids, reagents or samples into the gap 6.

This disposable cartridge 2 is configured for insertion into a cartridge accommodation site 8 of a digital microfluidics system 1 and comprises a rigid cover plate 12 with a lower surface 48'. The rigid cover plate 12 depicted is relatively thin (e.g. having a thickness of about 0.5 to 2 mm) and for better stabilization is attached to a lower surface 48 of a frame-like body 47. This disposable cartridge 2 also comprises at least one through hole 19 located at a loading site 41 of the cover plate 12 and a second hydrophobic surface 17'' that may be or may be not impermeable to liquids, the second hydrophobic surface 17'' at least being permeable to ions. This disposable cartridge 2 further comprises a bottom layer 3 with a first hydrophobic surface 17' that is impermeable to liquids and that is configured as a working film for manipulating samples in liquid droplets 23 thereon utilizing an electrode array 9 of the digital microfluidics system 1 when the bottom layer 3 of the disposable cartridge 2 is placed over said electrode array 9. This disposable cartridge 2 in addition comprises a gap 6 that is located between the first hydrophobic surface 17' of the bottom layer 3 and the second hydrophobic surface 17'' of the rigid cover plate 12.

This disposable cartridge 2 according to a tenth embodiment is characterized in that the bottom layer 3 is configured as a flexible film that is sealingly attached to the lower surface 48' of the rigid cover plate 12 along a circumference 40 of the flexible bottom layer 3. The flexible bottom layer 3 is configured to be attracted and spread over the uppermost surface 52 of a cartridge accommodation site 8 of the digital microfluidics system 1 by the underpressure in the evacuation space 46 of the digital microfluidics system 1. Thus, the disposable cartridge 2 is devoid of a spacer 5 that is located in the gap 6 between the flexible bottom layer 3 and the second hydrophobic surface 17'' of the rigid cover plate 12 for defining a particular distance between said first hydrophobic surface 17' and said second hydrophobic surface 17'' of the rigid cover plate 12.

Preferably, this disposable cartridge 2 comprises an electrically conductive material 15 that is attached to the lower surface 48' of the rigid cover plate 12. According to a preferred variant embodiment as shown, the electrically conductive material 15 is configured to provide the lower surface 48' of the rigid cover plate 12 with the second hydrophobic surface 17''. Alternatively however, a top layer 4 that comprises the second hydrophobic surface 17'' may be attached directly to the lower surface 48' of the rigid cover plate 12 or the lower surface 48' of the rigid cover plate 12 may be treated to be hydrophobic and thus, the rigid cover plate 12 itself providing the second hydrophobic surface 17'' (both not shown).

The FIG. 14 shows a section view of one disposable cartridge 2 before reaching its accommodation site 8, the disposable cartridge 2 being configured according to an eleventh embodiment and to be hold in place at the cartridge accommodation site 8 with or without a clamp. The depicted disposable cartridge 2 comprises a minimized number of elements in order to simplify the production costs for the disposable cartridge 2.

The disposable cartridge 2 according to this eleventh embodiment is configured for insertion into a cartridge accommodation site 8 of a digital microfluidics system 1 as herein disclosed. This disposable cartridge 2 comprises:

(a) a plane rigid cover plate 12 comprising a lower surface 48', at least one through hole 19 located at a loading site 41 and a second hydrophobic surface 17" that at least is permeable to ions;

(b) a bottom layer 3 with a first hydrophobic surface 17' that is impermeable to liquids and that is configured as a working film for manipulating samples in liquid droplets 23 thereon utilizing an electrode array 9 of the digital microfluidics system 1 when the bottom layer 3 of the disposable cartridge 2 is placed over said electrode array 9; and (c) a gap 6 that is located between the first hydrophobic surface 17' of the bottom layer 3 and the second hydrophobic surface 17" of the rigid cover plate 12.

The disposable cartridge 2 according to this eleventh embodiment is characterized in that the bottom layer 3 is configured as a flexible film that is sealingly attached to the lower surface 48' of the rigid cover plate 12 along a circumference 40 of the flexible bottom layer 3, the flexible bottom layer 3 being configured to be attracted and spread over the uppermost surface 52 of a cartridge accommodation site 8 of the digital microfluidics system 1 by the underpressure in the evacuation space 46 of the digital microfluidics system 1, the disposable cartridge 2 thus being devoid of a spacer 5 that is located in the gap 6 between the flexible bottom layer 3 and the second hydrophobic surface 17" of the rigid cover plate 12 for defining a particular distance between said first hydrophobic surface 17' and said second hydrophobic surface 17" of the rigid cover plate 12. This disposable cartridge 2 being further characterized in that the at least one through hole 19 of the rigid cover plate 12 is configured as a loading site 41 for transferring processing liquids, reagents or samples into the gap 6.

Preferably, the lower surface 48' of the cover plate 12 is configured as the second hydrophobic surface 17". It alternatively may be preferred that the cartridge 2 comprises a top layer 4 that provides the second hydrophobic surface 17" and that is attached to the lower surface 48' of the rigid cover plate 12 of the disposable cartridge 2. It may be preferred as a second alternative that the cartridge 2 comprises an electrically conductive material 15 that is attached to the lower surface 48' the rigid cover plate 12, the electrically conductive material 15 being configured to provide the lower surface 48' of the rigid cover plate 12 with the second hydrophobic surface 17".

The digital microfluidics system 1 that is shown in the FIGS. 13 and 14 has a similar construction like the digital microfluidics system 1 shown in the FIGS. 1-12. However, the particular embodiments that are depicted in the FIGS. 9-12 all comprise a number of suction holes 35, which are located at the cartridge accommodation site 8 of the base unit 7, and which simply penetrate the electrode array 9 and the bottom substrate 11 that carries the electrode array 9. Those embodiments of the FIGS. 9-12 comprise a number of vacuum lines 34 that directly lead to these suction holes 35 and that link these suction holes 35 to the vacuum source 33. In order to practically evenly distribute the underpressure within the evacuation space 46, in those embodiments as shown in the FIGS. 9-12, the suction holes 35 need to be practically evenly distributed over the area of the electrode array 9 and cartridge accommodation site 8.

The digital microfluidics system 1 as shown in the FIGS. 9-14 is suited for manipulating samples in liquid droplets within a gap 6 between a first hydrophobic surface 17' of a bottom layer 3 and a second hydrophobic surface 17" of at least one disposable cartridge 2 as shown in the FIGS. 9-14.

However, the digital microfluidics system 1 shown in the FIGS. 13 and 14 comprises a number of suction holes 35 that penetrate the bottom substrate 11, but not the electrode array 9. These suction holes 35 are preferably distributed in the cartridge accommodation site 8 around the area of the electrode array 9. In order to practically evenly distribute the underpressure within the evacuation space 46, the suction holes 35 are configured to mouth into suction channels 51, which suction channels 51 are arranged in the uppermost surface 52 of the cartridge accommodation site 8 of the digital microfluidics system 1. In the embodiment shown in the FIGS. 13 and 14, the uppermost surface 52 of the cartridge accommodation site 8 is provided by the dielectric layer 24 that is attached to the upper surface of the electrode array 9 and the bottom substrate 11. In consequence, the suction channels 51 are configured as grooves that are countersunk in the surface of the dielectric layer 24. The pattern of these suction channels 51 or grooves may comprise branched or un-branched straight lines, branched or un-branched meandering lines any combinations thereof. As shown, the suction channels 51 or grooves may reach over a part of the electrode array 11 and/or over a part of the bottom substrate 11. Deviating from the straight suction holes 35 as shown in the FIGS. 13 and 14, the suction holes 35 can penetrate the bottom substrate 11 in any arbitrary direction as best suited, e.g. the suction holes 35 can be configured to penetrate the bottom substrate 11 at an oblique angle or stepwise. Especially in a case where the bottom substrate 11 is configured to comprise two separate plates that are sandwiched on top of each other (not shown), stepwise and/or branched configuration of the suction holes 35 may be preferred in order to reduce complexity of the suction channels 51 or grooves in the surface of the dielectric layer 24.

In any case, it is preferred to arrange the suction channels 51 or grooves such that an even underpressure can be established in the evacuation space 46. As soon as the disposable cartridge 2 is located at the cartridge accommodation site 8, the gasket 36 seals in the cartridge accommodation site 8 the evacuation space 46, which is defined by the flexible bottom layer 3 of the disposable cartridge 2, the uppermost surface 52 of the cartridge accommodation site 8, and the gasket 36.

The suction holes 35 can be directly linked to the vacuum source 33 of the digital microfluidics system 1 by an appropriate number of vacuum lines 34 (see FIGS. 9-12). Alternatively, the suction holes 35 may be configured to mouth into a vacuum space 50, which vacuum space 50 is arranged at the at least one cartridge accommodation site 8 and under the electrode array 9 and/or the bottom substrate 11. Preferably, the vacuum space 50 is connected to the vacuum source 33 of the digital microfluidics system 1 by at least one vacuum line 34 (see FIGS. 13 and 14).

As in all other embodiments previously shown, the flexible bottom layer 3 preferably is configured as a monolayer or single layer, respectively of a hydrophobic material. According to a first preferred alternative variant, the flexible bottom layer 3 is configured as a monolayer or single layer, respectively of electrically non-conductive material, an upper surface of the flexible bottom layer 3 being treated to be a hydrophobic surface 17. According to a second preferred alternative variant, the flexible bottom layer 3 is configured as a laminate comprising a lower layer and a hydrophobic upper layer, the lower layer being electrically conductive or non-conductive.

In another alternative embodiment, the disposable cartridge 2 further comprises a gasket 36 that is attached to a lower surface and along a circumference 40 of the flexible bottom layer 3. The gasket 36 thus defining a particular distance between said first hydrophobic surface 17' and said second hydrophobic surface 17", when the disposable cartridge 2 is placed over an electrode array 9 of a digital microfluidics system 1, if said digital microfluidics system 1 is equipped with suction holes 35 in the electrode array 9, and if the flexible bottom layer 3 is aspirated by said suction holes 35.

In the FIG. 12, the gasket 36 is attached to the bottom substrate 11 that supports the individual electrodes 10 of the electrode array 9. Here, a dielectric layer 24 is attached to the surface of the electrode array 9, protecting the individual electrodes from oxidation, mechanical impact and other influences like contamination. The dielectric layer 24 also covers the gasket 36 that is configured as a closed ring that extends around the accommodation site 8 for the disposable cartridge 2. The dielectric layer 24 further covers at least a part of the insertion guide 25 and reaches over a part (see left side) or beyond the entire height of the disposable cartridge 2 (see right side).

According to the seventh, eighth, and ninth embodiment of the of the disposable cartridge 2 of the present invention described so far, it is also proposed an alternative digital microfluidics system that is configured to take up at least one of these inventive disposable cartridges 2 in its cartridge accommodation sites 8 located on the electrode array 9 of the base unit 7. Such a digital microfluidics system 1 for manipulating samples in liquid droplets within the gap 6 between the flexible bottom layer 3 and the top layer 4 of at least one such disposable cartridge 2 preferably comprises:
(a) a base unit 7 with at least one cartridge accommodation site 8 that is configured for taking up the disposable cartridge 2;
(b) an electrode array 9 located at said cartridge accommodation site 8 of the base unit 7, the electrode array 9 being supported by a bottom substrate 11 and substantially extending in a first plane and comprising a number of individual electrodes 10; and
(c) a central control unit 14 for controlling the selection of the individual electrodes 10 of said electrode array 9 and for providing these electrodes 10 with individual voltage pulses for manipulating liquid droplets within the gap 6 of said cartridge 2 by electrowetting.

The inventive digital microfluidics system 1 further comprises:
(d) a number of suction holes 35 that penetrate the electrode array 9 and that are distributed over the cartridge accommodation site 8 of the base unit 7;
(e) a vacuum source 33 for establishing an underpressure in an evacuation space 46; and
(f) a number of vacuum lines 34 that link the suction holes 35 to the vacuum source 33.

The inventive digital microfluidics system 1 is characterized in that a gasket 36, when located around a circumference 45 of the cartridge accommodation site 8, seals in the cartridge accommodation site 8 the evacuation space 46, which is defined by the flexible bottom layer 3 of the disposable cartridge 2, the electrode array 9 and the bottom substrate 11 of the digital microfluidics system 1, and the gasket 36.

The inventive digital microfluidics system 1 is further characterized in that the underpressure in the evacuation space 46 causes the flexible bottom layer 3 of the disposable cartridge 2 that is placed on the cartridge accommodation site 8 to be attracted and spread over the electrode array 9 and bottom substrate 11 of the digital microfluidics system 1. It is expressly noted that the gap 6 defined by this spreading the flexible bottom layer 3 of the disposable cartridge 2 is enabled without the use of a spacer 5 located between the flexible bottom layer 3 and the top layer 4 of the disposable cartridge 2.

According to another variant of the seventh and eighth embodiment of the disposable cartridge 2 of the present invention, the disposable cartridge 2 does not comprise a gasket 36. Instead, the gasket 36 is permanently fixed to the bottom substrate 11 of the base unit 7 of the digital microfluidics system 1, or the gasket 36 is fixed to a dielectric layer 24 that permanently covers the electrode array 9 and the bottom substrate 11. Of course in this case, the dielectric layer 24 has holes at the sites of the suction holes 35 of the base unit 7 in order to enable formation of the underpressure in the evacuation space 46, which causes the flexible bottom layer 3 of the disposable cartridge 2 that is placed on the cartridge accommodation site 8 to be attracted and spread over the electrode array 9 and bottom substrate 11 of the digital microfluidics system 1.

According to a further variant of the seventh and eighth embodiment of the disposable cartridge 2 of the present invention, the gasket 36 is permanently attached to a lower surface and along a circumference 40 of the flexible bottom layer 3 of a disposable cartridge 2 to be placed on the cartridge accommodation site 8 of the base unit 7.

The inventive digital microfluidics system 1 preferably is equipped with a base unit 7, which comprises an insertion guide 25 that is configured as a frame, which is sized to accommodate a disposable cartridge 2 therein. It is especially preferred that the base unit 7 comprises a clamp 37 that is configured to fix this disposable cartridge 2 at a desired position on the cartridge accommodation site 8 of the base unit 7. As demonstrated in connection with the ninth embodiment (see FIG. 12), there is no absolute need for using such a clamp 37. Here, the layers are all sealed well and the vacuum in the evacuation space 46 on the bottom surface holds the disposable cartridge 2 safely in place and within the cartridge accommodation site 8 of the digital microfluidics system 1.

It is further preferred that the base unit 7 comprises actuating elements 38 that are configured for actuating plungers 42 that in each case are configured to be movable within a compartment 21 of a disposable cartridge 2 that is placed on the cartridge accommodation site 8. Thus, the plungers 42 in each case are configured for pressing the content of the respective compartment 21 into the gap 6 of the disposable cartridge 2 that is located on the cartridge accommodation site 8 of the base unit 7. Preferably, the actuating elements 38 are configured to be motor driven and controlled by the central control unit 14 of the digital microfluidics system 1. The insertion guide 25 preferably is manufactured from aluminum, from another light metal or light alloy, or from stainless steel. The following materials and dimensions are especially preferred for manufacturing a disposable cartridge 2 of the present invention:

TABLE 1

| Part | No. | Material | Dimensions and Shape |
|---|---|---|---|
| Bottom layer | 3 | Fluorinated ethylene propylene (FEP), Cyclo olefin polymer (COP) | Foil: 8-50 μm |

TABLE 1-continued

| Part | No. | Material | Dimensions and Shape |
|---|---|---|---|
| Top layer | 4 | Al foil | Foil: 20-100 μm |
| Gap | 6 | — | Height: 0.2-2.0 mm; preferably 0.5 mm |
| Electrodes | 10 | Al; Cu; Au; Pt | Plating: 1.5 × 1.5 mm |
| Cover plate | 12 | Mylar ®; acrylic | Foil, plate: 0.15-1.8 mm; preferably 1.5 mm |
| Electrically conductive material | 15 | Au, Pt, TIO, PP, PA | Layer: 20-100 μm; preferably 50 μm |
| 1$^{st}$ hydrophobic surface | 17' | COP, FEP | Foil: 8-50 μm |
| 2$^{nd}$ hydrophob. surface | 17" | Teflon ® | Spin coating: 5-500 nm; preferably 20 nm |
| Liquid droplet | 23 | — | Volume: 0.1-5 μl |
| Dielectric layer | 24 | Fluorinated ethylene propylene, FEP | Foil or casting: 20-100 μm |
| Insertion guide | 25 | Al; Al/Mg; steel; PTFE | Frame: 5-30 mm |
| Gasket | 36 | Synthetic or natural rubber | Frame: 0.2-2.0 mm; preferably 0.5 mm |
| Seal, 1$^{st}$ type, compliant seal | 39 | Natural rubber or Neoprene ® | O-ring: 5-10 mm; preferably 7 mm |
| Seal, 2$^{nd}$ type, stiff seal | 39' | Viton ® | O-ring: 3-8 mm; preferably 4 mm |
| Capillary orifice | 41" | — | Diameter: 0.1-0.5 mm |
| Pipetting orifice | 41'" | — | Diameter: 0.3-3.0 mm |
| Elastic layer | 44 | Synthetic or natural rubber | Foil: 0.5-2.0 mm |
| Body | 47 | Polypropylene, PP | 65 × 85 mm; 6-25 mm |

The inventive disposable cartridge 2 and the inventive digital microfluidics system 1 enable an alternative method for manipulating samples in liquid droplets 23 that adhere to a hydrophobic surface 17 to be carried out. This method comprising the steps of:

(a) providing a disposable cartridge 2 with a first hydrophobic surface 17' of a bottom layer 3, with a second hydrophobic surface 17" of a top layer 4, and with a gap 6 between the first and second hydrophobic surfaces 17',17", the disposable cartridge 2 further comprising a body 47 with at least one compartment 21 to therein hold processing liquids, reagents or samples, said compartment 21 comprising a through hole 19 for delivering at least some of its content to the gap 6;

(b) providing a digital microfluidics system 1 with an electrode array 9 that substantially extends in a first plane and that comprises a number of individual electrodes 10 supported by a bottom substrate 11 and connected to a central control unit 14 of the digital microfluidics system 1 for controlling the selection of individual electrodes 10 of said electrode array 9 and for providing these electrodes 10 with individual voltage pulses for manipulating said liquid droplets 23 on said first hydrophobic surface 17' by electrowetting; and (c) defining the gap 6 so that the hydrophobic surface 17" of the top layer 4 extends substantially parallel to and in a distance to said first hydrophobic surface 17' of the bottom layer 3.

This method is characterized in that it comprises the steps of:

(d) providing the bottom layer 3 as a flexible film that is sealingly attached to the top layer 4 along a circumference 40 of the flexible bottom layer 3, the disposable cartridge 2 thus being devoid of a spacer 5 that is located between the flexible bottom layer 3 and the top layer 4 for defining a particular distance between said first hydrophobic surface 17' and said second hydrophobic surface 17";

(e) placing the disposable cartridge 2 on a cartridge accommodation site 8 of a base unit 7 of the digital microfluidics system 1, the top layer 4 being configured to provide a seal between a lower end of at least one compartment 21 and the gap 6, and the top layer 4 comprising loading sites 41 for transferring processing liquids, reagents or samples into the gap 6;

(f) sealing in the cartridge accommodation site 8 an evacuation space 46 by a gasket 36 located around a circumference 45 of the cartridge accommodation site 8, the evacuation space 46 being defined by the flexible bottom layer 3, the electrode array 9, the bottom substrate 11, and the gasket 36; and (g) creating in the evacuation space 46 an underpressure, which causes the flexible bottom layer 3 of the disposable cartridge 2 that is placed on the cartridge accommodation site 8 to be attracted and spread over the electrode.

When applying this method, preferably the underpressure in the evacuation space 46 is created by a vacuum source 33, which is controlled by the central control unit 14 of the digital microfluidics system 1, and which is linked by a number of vacuum lines 34 to suction holes 35 that penetrate the electrode array 9 and that are distributed over the cartridge accommodation site 8 of the base unit 7. It is further preferred that a plunger 42 contained in a compartment 21 of the disposable cartridge 2 is moved manually or by an actuating element 38 and the content of the respective compartment 21 is pressed against a respective loading site 41 of the top layer 4. It is also preferred that with a piercing pin 27 of the plunger 42, the top layer 4 is pierced at a respective piercing site 41' of the compartment 21 and some of the content of the compartment 21 is pressed through a hole punched into this piercing site 41' of the top layer 4 and into the gap 6. Alternatively or additionally, it is also preferred that some of the content of the compartment 21 is pressed with the plunger 42 through a respective capillary orifice 41" of the top layer 4 and into the gap 6, the capillary orifice 41" being sized to exhibit capillary forces that prevent flowing though of aqueous liquids without a pressure being applied with the plunger 42.

In the attached FIGS. 15 to 17, especially preferred embodiments of a disposable cartridge according to a twelfth embodiment are shown in partial sections. In each case, the disposable cartridge 2 is located at its accommodation site 8 of the digital microfluidics system 1. The disposable cartridge 2 in each case comprises (a) a bottom layer 3 with a first hydrophobic surface 17' that is impermeable to liquids and that is configured as a working film for manipulating samples in liquid droplets 23 thereon utilizing an electrode array 9 of a digital microfluidics system 1 when the bottom layer 3 of the disposable cartridge 2 is placed over said electrode array 9;

(b) a rigid cover plate 12 with a lower, second hydrophobic surface 17", an upper surface 58, and at least one through hole 19; and (c) a gap 6 that is located between the first hydrophobic surface 17' of the bottom layer 3 and the second hydrophobic surface 17" of the rigid cover plate 12.

The bottom layer 3 in each case is configured as a flexible film that is sealingly attached to the lower, second hydrophobic surface 17" of the rigid cover plate 12. Thus, the disposable cartridge is devoid of a spacer located between the flexible bottom layer 3 and the rigid cover plate 12 for defining a particular distance between the first hydrophobic surface 17' and the second hydrophobic surface 17". Preferably, the flexible bottom layer 3 is sealingly attached around its circumference 40 to the lower surface 17' of the rigid cover plate 12. Preferably, the gap 6 is at least partially filled with oil 53 when manipulating droplets 23 on the bottom layer 3.

Preferably, the upper surface 58 of the rigid cover plate 12 is at least partially covered with a peel-off protection film 54 or with a pierceable membrane 31 that also functions as a protection film which is hindering contamination of the through holes 19 form the outside and hindering contamination of the surroundings by the content of the gap 6 of the disposable cartridge 2.

The digital microfluidics system 1 for manipulating samples in liquid droplets 23 within the gap 6 between the first hydrophobic surface 17' of the bottom layer 3 and the second hydrophobic surface 17" of the rigid cover plate 12 of the disposable cartridge depicted in the FIGS. 15 to 17 comprises:

(a) a base unit 7 with at least one cartridge accommodation site 8 that is configured for taking up one disposable cartridge 2;
(b) an electrode array 9 located at said at least one cartridge accommodation site 8 of the base unit 7, the electrode array 9 being supported by a bottom substrate 11 and substantially extending in a first plane and comprising a number of individual electrodes 10;
(c) a central control unit 14 for controlling the selection of the individual electrodes 10 of said electrode array 9 and for providing these electrodes 10 with individual voltage pulses for manipulating liquid droplets 23 within the gap 6 of said cartridge 2 by electrowetting;
(d) a number of suction holes 35 in the electrode array 9, the suction holes 35 mouthing into a vacuum space 50 of the bottom substrate 11;
(e) a vacuum source 33 for establishing an underpressure in an evacuation space 46; and
(f) a number of vacuum lines 34 (i.e. one or more vacuum lines 34) that link the vacuum space 50 to the vacuum source 33.

The digital microfluidics system 1 depicted in the FIGS. 15 to 17 comprises a rigid spacer 5 for defining a particular distance between said first hydrophobic surface 17' and said second hydrophobic surface 17" independently of the level of screwing or clamping and thereby pressing the cartridge onto the rigid spacer 5. The digital microfluidics system 1 depicted in the FIGS. 15 to 17 further comprises an insertion guide 25 configured as a frame for centering a disposable cartridge 2 at said cartridge accommodation site 8, for holding down the disposable cartridge 2 to the rigid spacer 5, and for sealing an evacuation space 46 by first and second seals 39,39' of the frame. With respect to an inserted cartridge 2, the frame 25 leaves open a small cleft around the circumference 45 of the cartridge accommodation site 8. The digital microfluidics system 1 further comprises an evacuation space 46, which is defined by the flexible bottom layer 3 of the disposable cartridge 2, an uppermost surface 52 of the cartridge accommodation site 8, and the frame 25 with the seals 39,39'. As in the other embodiments of the digital microfluidics system 1 shown before, the underpressure in the evacuation space 46 causes the flexible bottom layer 3 that is placed at the cartridge accommodation site 8 to be attracted to and spread over the uppermost surface 52 of the cartridge accommodation site 8 of the digital microfluidics system 1.

Preferably in the embodiment as shown in the FIGS. 15 to 17, the electrode array or PCB 9 is not covered by a dielectric layer 24 like in the FIGS. 11 and 12, but unlike the embodiments of the FIGS. 2-6, 8-10, and 13-14. Thus, the electrodes 10 of the PCB 9 are bare metal and in consequence, the flexible bottom layer 3 or working film of the disposable cartridge comprises a dielectric layer with a hydrophobic surface 17' or a laminate of a dielectric layer and a hydrophobic layer on top. Alternatively, the flexible bottom layer 3 is configured as a monolayer or single layer, respectively of electrically non-conductive material, the upper surface 17' of the flexible bottom layer 3 being treated to be hydrophobic.

Preferably, at least some of the suction holes 35 in the electrode array 9 are configured as conductive through-holes that penetrate the PCB 9 for contacting at least some of the individual electrodes 10 to the central control unit 14. These conductive through-holes or vacuum vias in the PCB 9 may be made conductive by electroplating or by lining with a tube or rivet.

Preferably to effectively seal the evacuation space 46, seals 39,39' are of two different types, comprising i.e. a different material and/or cross section. A number of first type seals 39 (drawn larger in the FIGS. 15 to 17) are of a very compliant material that is largely deformed, in consequence, the seal bearing parts (e.g. the frame 25 and the bottom structure 11) are firmly pressed against the respective counter part (i.e. the top and bottom side of the PCB 9). Preferred materials for this compliant seals 39 are O-rings of natural rubber or of a DuPont Elastomer such as Neoprene®. Alternatively (not shown), the first type seals 39 may be configured as a lip seal.

Preferably, a second type of a seal 39' is of a material that is less compliant and stiff enough to undergo only a minimal compression and thus combining the task of sealing the evacuation space 46 and of pressing the disposable cartridge 2 firmly against the rigid spacer 5. Preferred materials for this stiff seal 39' are e.g. O-rings of a DuPont Performance Elastomer such as Viton®.

In FIG. 15, the disposable cartridge 2 is centered in the cartridge accommodation site 8 by a frame 25 and pressed on a rigid spacer 5 of the PCB 9 with a closing means 30 that is configured as a pressing plate. The reference numbers 57 point to the screw holes in the bottom structure 11, PCB 9, Frame 25, and pressing plate 30. Between the pressing plate 30 and the frame 25 another first type compliant seal 39 is located for safely sealing the evacuation space 46. If required, at least one through hole 19 in the rigid cover plate 12 can be utilized as a loading site 41 for samples. The digital microfluidics system 1 may be equipped with an optical detection device 55 and the PCB 9 can be additionally supported by support posts 56, thus allowing optical analysis of samples inside of the gap 6 of the disposable cartridge 2.

In FIG. 16, the disposable cartridge 2 is centered in the cartridge accommodation site 8 and pressed on a rigid spacer 5 of the PCB 9 by a frame profile that acts the same time as an insertion guide 25 and as a closing means 30. Here, the frame profile is screwed to the PCB 9 and to the bottom structure 11 of the digital microfluidics system 1. The reference numbers 57 point to the screw holes in the bottom structure 11, PCB 9, and frame profile 25,30. Alternatively (not shown), the frame profile may be pressed down to the PCB 9 and to the bottom structure 11 of the digital microfluidics system 1 by a clamp 37 (comparable to FIG. 17). If required, at least one through holes 19 in the rigid cover plate 12 can be utilized as a pipetting orifice 41''' for filling samples into the gap 6 or for withdrawing samples from the gap 6 with a piercing pipette tip 20 or with a disposable pipette tip 26, thus allowing analysis of samples outside of the gap 6 of the disposable cartridge 2 and in an separate analysis system.

In FIG. 17, the disposable cartridge 2 is centered in the cartridge accommodation site 8 by a screwed frame 25 and pressed on a rigid spacer 5 of the PCB 9 with a closing means 30 that is configured as a pressing plate. The reference numbers 57 point to the screw holes in the bottom structure 11, PCB 9, and Frame 25. Between the pressing plate 30 and the frame 25 another first type compliant seal 39 is located for safely sealing the evacuation space 46. The pressing plate 30 may be pressed down to the frame 25 and to the inserted cartridge 2 by a clamp 37. If required, at least one through hole 19 in the rigid cover plate 12 can be utilized as a loading site 41 for samples. The digital microfluidics system 1 may be equipped with an optical detection device 55 and the PCB 9 can be additionally supported by support posts 56, thus allowing optical analysis of samples inside of the gap 6 of the disposable cartridge 2.

In each case it is preferred that after manipulating liquid droplets 23 on said first hydrophobic surface 17' by electrowetting and/or analyzing the sample in some of these liquid droplets 23, the disposable cartridge 2 is taken from the cartridge accommodation site 8 of the base unit 7 of the digital microfluidics system 1 and discarded.

Any combination of the features of the different embodiments of the cartridge 2 disclosed herein that appear reasonable to a person of skill are comprised by the gist and scope of the present invention.

Even if they are not particularly described in each case, the reference numbers refer to similar elements of the digital microfluidics system 1 and in particular of the disposable cartridge 2 of the present invention.

| Reference numbers: | |
|---|---|
| 1 | digital microfluidics system |
| 2 | disposable cartridge |
| 3 | flexible bottom layer |
| 4 | top layer |
| 5 | spacer, rigid spacer |
| 6 | gap, gap between 3 and 4 |
| 7 | base unit |
| 8 | cartridge accommodation site |
| 9 | electrode array, PCB |
| 10 | individual electrode |
| 11 | bottom substrate |
| 12 | cover plate; rigid cover plate |
| 13 | top substrate |
| 14 | central control unit |
| 15 | electrically conductive material |
| 16 | hinge |
| 17 | hydrophobic surface |
| 17' | $1^{st}$ hydrophobic surface |
| 17" | $2^{nd}$ hydrophobic surface |
| 18 | piercing facility |
| 19 | through hole |
| 20 | piercing pipette tip |
| 21 | compartment |
| 22 | additional piercing facility |
| 23 | liquid droplet |
| 24 | dielectric layer |
| 25 | insertion guide, frame |
| 26 | disposable pipette tip, pipette tip |
| 27 | piercing pin |
| 28 | pin plate |
| 29 | displacement portion |
| 30 | closing means, pressing plate |
| 31 | pierceable membrane |
| 32 | separating bar |
| 33 | vacuum source |
| 34 | vacuum line |

-continued

| Reference numbers: | |
|---|---|
| 35 | suction hole |
| 36 | gasket |
| 37 | clamp |
| 38 | actuating element |
| 39 | seal, $1^{st}$ type, compliant seal |
| 39' | seal, $2^{nd}$ type, stiff seal |
| 40 | circumference of 3 |
| 41 | loading site |
| 41' | piercing site |
| 41" | capillary orifice |
| 41''' | pipetting orifice |
| 42 | plunger |
| 43 | central opening |
| 44 | elastic layer |
| 45 | circumference of 8 |
| 46 | evacuation space |
| 47 | body |
| 48 | lower surface of 47 |
| 48' | lower surface of 12 |
| 49 | upper surface of 47 |
| 50 | vacuum space |
| 51 | suction channels |
| 52 | uppermost surface of 8 |
| 53 | oil |
| 54 | peel-off protection film |
| 55 | optical detection device |
| 56 | support post |
| 57 | screw holes |
| 58 | upper surface of 12 |

What is claimed is:

1. A digital microfluidics system (1) for manipulating samples in liquid droplets within a gap (6) between a first hydrophobic surface (17') of a bottom layer (3) and a second hydrophobic surface (17") of at least one disposable cartridge (2), the digital microfluidics system (1) comprising:

(a) a base unit (7) with at least one cartridge accommodation site (8) that is configured for taking up said at least one disposable cartridge (2);

(b) an electrode array (9) located at said at least one cartridge accommodation site (8) of the base unit (7), the electrode array (9) being supported by a bottom substrate (11), substantially extending in a first plane and comprising a number of individual electrodes (10); and (c) a central control unit (14) for controlling the selection of the individual electrodes (10) of said electrode array (9) and for providing these electrodes (10) with individual voltage pulses for manipulating liquid droplets (23) within the gap (6) of said at least one disposable cartridge (2) by electrowetting, wherein the digital microfluidics system (1) further comprises:

(d) a number of suction holes (35) that penetrate the electrode array (9) and/or the bottom substrate (11) and that are located at the at least one cartridge accommodation site (8) of the base unit (7);

(e) a vacuum source (33) for establishing an underpressure in at least one of an evacuation space (46) and a vacuum space (50); and (f) a number of vacuum lines (34) that link the suction holes (35) and/or vacuum space (50) to the vacuum source (33);

wherein a gasket (36) or a number of seals (39,39'), when the at least one disposable cartridge (2) is located at the at least one cartridge accommodation site (8), seal in said at least one cartridge accommodation site (8) the evacuation space (46), which is defined by a flexible bottom layer (3) of the at least one disposable cartridge (2), an uppermost surface (52) of the at least one cartridge accommodation site (8), and the gasket (36) or the seals (39,39') which are supported by an insertion guide and closing means (25,30); and wherein the underpressure in the evacuation space (46) causes the flexible bottom layer (3) of the at least one disposable cartridge (2) that is placed at the at least one cartridge accommodation site (8) to be attracted and spread over the uppermost surface (52) of the at least one cartridge accommodation site (8) of the digital microfluidics system (1).

2. The digital microfluidics system (1) of claim 1, wherein the gasket (36) is dimensioned to define a height of the gap (6) between the first hydrophobic surface (17') of the bottom layer (3) and the second hydrophobic surface (17") of the at least one disposable cartridge (2).

3. The digital microfluidics system (1) of claim 1, wherein the electrode array (9) of the digital microfluidics system (1) comprises a rigid spacer (5) that is dimensioned to define a height of the gap (6) between the first hydrophobic surface (17') of the bottom layer (3) and the second hydrophobic surface (17") of the at least one disposable cartridge (2).

4. The digital microfluidics system (1) of claim 1, wherein the suction holes (35) are configured to mouth into suction channels (51), said suction channels (51) being arranged in the uppermost surface (52) of the at least one cartridge accommodation site (8) of the digital microfluidics system (1).

5. The digital microfluidics system (1) of claim 1, wherein the suction holes (35) are configured to mouth into a vacuum space (50), said vacuum space (50) being arranged at the at least one cartridge accommodation site (8) and under the electrode array (9) in the bottom substrate (11), said vacuum space (50) being connected to the vacuum source (33) of the digital microfluidics system (1) by at least one of the vacuum lines (34).

6. The digital microfluidics system (1) of claim 1, wherein the uppermost surface (52) of the at least one cartridge accommodation site (8) comprises a dielectric layer (24) that covers the electrode array (9), the dielectric layer (24) having holes at the sites of the of suction holes (35) of the base unit (7).

7. The digital microfluidics system (1) of claim 1, wherein the gasket (36) is permanently fixed to the electrode array (9) of the at least one cartridge accommodation site (8) of the base unit (7) of the digital microfluidics system (1).

8. The digital microfluidics system (1) of claim 6, wherein the gasket (36) is fixed to the dielectric layer (24) that permanently covers the electrode array (9) of the at least one cartridge accommodation site (8) of the digital microfluidics system (1).

9. The digital microfluidics system (1) of claim 6, wherein the gasket (36) is permanently fixed to the bottom substrate (11) that supports the electrode array (9); the dielectric layer (24) permanently covering the bottom substrate (11), the electrode array (9), and the gasket (36).

10. The digital microfluidics system (1) of claim 1, wherein the base unit (7) comprises an insertion guide (25) that is configured as a frame, which is sized to accommodate the at least one disposable cartridge (2) therein.

11. The digital microfluidics system (1) of claim 3, wherein the base unit (7) comprises a closing means (30) that is configured as a pressing plate for pressing the at least one disposable cartridge (2) to the rigid spacer (5) of the electrode array (9) of the digital microfluidics system (1).

12. The digital microfluidics system (1) of claim 1, wherein the base unit (7) comprises a clamp (37) that is configured to fix the at least one disposable cartridge (2) at a desired position of the at least one cartridge accommodation site (8) of the base unit (7).

13. A disposable cartridge (2) that is configured for insertion into a cartridge accommodation site (8) of a digital microfluidics system (1) according to claim 1, the disposable cartridge (2) comprising:
 (a) a body (47) with at least one compartment (21) configured to hold therein processing liquids, reagents or samples, at least one of said compartments (21) comprising a through hole (19) for delivering at least some of its content;
 (b) a bottom layer (3) with a first hydrophobic surface (17') that is impermeable to liquids and that is configured as a working film for manipulating samples in liquid droplets (23) thereon utilizing an electrode array (9) of the digital microfluidics system (1) when the bottom layer (3) of the disposable cartridge (2) is placed over said electrode array (9);
 (c) a top layer (4) with a second hydrophobic surface (17") that is attached to a lower surface (48) of the body (47) of the disposable cartridge (2) and that at least is permeable to ions; and
 (d) a gap (6) that is located between the first hydrophobic surface (17') of the bottom layer (3) and the second hydrophobic surface (17") of the top layer (4),
wherein the bottom layer (3) is configured as a flexible film that is sealingly attached to the top layer (4) or to the body (47) along a circumference (40) of the flexible bottom layer (3), the flexible bottom layer (3) being configured to be attracted and spread over the uppermost surface (52) of a cartridge accommodation site (8) of the digital microfluidics system (1) by the underpressure in the evacuation space (46) of the digital microfluidics system (1), the disposable cartridge (2) thus being devoid of a spacer (5) that is located in the gap (6) between the flexible bottom layer (3) and the top layer (4) for defining a particular distance between said first hydrophobic surface (17') and said second hydrophobic surface (17").

14. The disposable cartridge (2) of claim 13,
 wherein the top layer (4) is configured to provide a seal between a lower end of at least one compartment (21) and the gap (6), the top layer (4) comprising loading sites (41) for transferring processing liquids, reagents or samples into the gap (6).

15. The disposable cartridge (2) of claim 14,
 which comprises at least one plunger (42) that in each case is configured to be movable within a compartment (21) manually or by an actuating element (38) for pressing the content of the respective compartment (21) against a respective loading site (41) of the top layer (4).

16. The disposable cartridge (2) of claim 14,
 wherein to an upper surface (49) of the body (47) of the disposable cartridge (2) is sealingly applied an elastic layer (44) that is configured to seal at least one of the compartments (21) against said upper surface (49).

17. The disposable cartridge (2) of claim 14,
 wherein the disposable cartridge (2) further comprises a plane rigid cover plate (12) that is attached to the lower surface (48) of the body (47) of the disposable cartridge (2), the top layer (4) being attached to said rigid cover plate (12), which rigid cover plate (12) comprising through holes (19) located at loading sites (41) of the top layer (4).

18. The disposable cartridge (2) of claim 14, which is configured as a plate-like structure with a lower surface (48), in each case the compartments (21) leading to said lower surface (48) with a through hole (19) at piercing sites (41') or capillary orifices (41").

19. A disposable cartridge (2) that is configured for insertion into a cartridge accommodation site (8) of a digital microfluidics system (1) according to claim 1, the disposable cartridge (2) comprising:
   (a) a body (47) with a lower surface (48), an upper surface (49), and at least one through hole (19);
   (b) a bottom layer (3) with a first hydrophobic surface (17') that is impermeable to liquids and that is configured as a working film for manipulating samples in liquid droplets (23) thereon utilizing an electrode array (9) of the digital microfluidics system (1) when the bottom layer (3) of the disposable cartridge (2) is placed over said electrode array (9);
   (c) an electrically conductive material (15) attached to the lower surface (48) of the body (47), the electrically conductive material (15) being configured to provide the lower surface (48) of the body (47) with a second hydrophobic surface (17"); and
   (d) a gap (6) that is located between the first hydrophobic surface (17') of the bottom layer (3) and the second hydrophobic surface (17") of the electrically conductive material (15),
wherein the bottom layer (3) is configured as a flexible film that is sealingly attached to the lower surface (48) of the body (47) along a circumference (40) of the flexible bottom layer (3), the flexible bottom layer (3) being configured to be attracted and spread over the uppermost surface (52) of a cartridge accommodation site (8) of the digital microfluidics system (1) by the underpressure in the evacuation space (46) of the digital microfluidics system (1), the disposable cartridge (2) thus being devoid of a spacer (5) that is located in the gap (6) between the flexible bottom layer (3) and the body (47) for defining a particular distance between said first hydrophobic surface (17') and said second hydrophobic surface (17").

20. A disposable cartridge (2) that is configured for insertion into a cartridge accommodation site (8) of a digital microfluidics system (1) according to claim 1, the disposable cartridge (2) comprising:
   (a) a plane rigid cover plate (12) comprising a lower surface (48'), at least one through hole (19) located at a loading site (41) and a second hydrophobic surface (17");
   (b) a bottom layer (3) with a first hydrophobic surface (17') that is impermeable to liquids and that is configured as a working film for manipulating samples in liquid droplets (23) thereon utilizing an electrode array (9) of the digital microfluidics system (1) when the bottom layer (3) of the disposable cartridge (2) is placed over said electrode array (9); and
   (c) a gap (6) that is located between the first hydrophobic surface (17') of the bottom layer (3) and the second hydrophobic surface (17") of the rigid cover plate (12),
wherein the bottom layer (3) is configured as a flexible film that is sealingly attached to the lower surface (48') of the rigid cover plate (12) along a circumference (40) of the flexible bottom layer (3), the flexible bottom layer (3) being configured to be attracted and spread over the uppermost surface (52) of a cartridge accommodation site (8) of the digital microfluidics system (1) by the underpressure in the evacuation space (46) of the digital microfluidics system (1), the disposable cartridge (2) thus being devoid of a spacer (5) that is located in the gap (6) between the flexible bottom layer (3) and the second hydrophobic surface (17") of the rigid cover plate (12) for defining a particular distance between said first hydrophobic surface (17') and said second hydrophobic surface (17") of the rigid cover plate (12).

21. The disposable cartridge (2) of claim 19, wherein the at least one through hole (19) of the body (47) or of the rigid cover plate (12) is configured as a loading site (41) for transferring processing liquids, reagents or samples into the gap (6).

22. The disposable cartridge (2) of claim 19, wherein the cartridge (2) comprises a top layer (4) that provides the second hydrophobic surface (17") and that is attached to the lower surface (48') of the rigid cover plate (12) of the disposable cartridge (2).

23. The disposable cartridge (2) of claim 19,
   wherein the cartridge (2) comprises an electrically conductive material (15) that is attached to the lower surface (48') of the rigid cover plate (12), the electrically conductive material (15) being configured to provide the lower surface (48') of the rigid cover plate (12) with the second hydrophobic surface (17").

24. The disposable cartridge (2) of claim 13, which further comprises a gasket (36) that is attached to the lower surface (48) of the body (47) or to the lower surface (48') of the rigid cover plate (12), and along a circumference (40) of the flexible bottom layer (3), the gasket (36) defining a particular distance between said first hydrophobic surface (17') and said second hydrophobic surface (17"), when the disposable cartridge (2) is placed over an electrode array (9) of a cartridge accommodation site (8) of the digital microfluidics system (1), if said digital microfluidics system (1) is equipped with suction holes (35) in the electrode array (9), and if the flexible bottom layer (3) is aspirated by said suction holes (35).

25. The disposable cartridge (2) of claim 13, wherein the loading sites (41) are selected from a group comprising piercing sites (41'), capillary orifices (41"), and pipetting orifices (41'").

26. The disposable cartridge (2) of claim 19, wherein the lower surface (48') of the cover plate (12) is configured as the second hydrophobic surface (17") that at least is permeable to ions.

27. The disposable cartridge (2) of claim 13, wherein the flexible bottom layer (3) is configured as a single layer of a hydrophobic material.

28. The disposable cartridge (2) of claim 13, wherein the flexible bottom layer (3) is configured as a single layer of electrically non-conductive material, an upper surface of the flexible bottom layer (3) being treated to be a hydrophobic surface (17).

29. The disposable cartridge (2) of claim 13, wherein the flexible bottom layer (3) is configured as a laminate comprising a lower layer and a hydrophobic upper layer, the lower layer being electrically non-conductive.

30. A method for manipulating samples in liquid droplets (23) that adhere to a hydrophobic surface (17) of a working film, the method comprising the steps of:
   (a) providing a disposable cartridge (2) with a first hydrophobic surface (17') of a bottom layer (3), with a second hydrophobic surface (17"), and with a gap (6) between the first and second hydrophobic surfaces (17',17"), the disposable cartridge (2) further comprising a body (47) and/or a plane rigid cover plate (12), and at least one through hole (19) for delivering processing liquids, reagents or samples to the gap (6);
   (b) providing a digital microfluidics system (1) with at least one electrode array (9) that substantially extends in a first plane and that comprises a number of individual electrodes (10) supported by a bottom substrate (11) and connected to a central control unit (14) of the digital microfluidics system (1) for controlling the selection of individual electrodes (10) of said electrode array (9) and for providing these electrodes (10) with individual voltage pulses for manipulating said liquid droplets (23) on said first hydrophobic surface (17') by electrowetting; and (c) defining the gap (6) so that the hydrophobic surface (17") extends substantially parallel to and in a distance to said first hydrophobic surface (17') of the bottom layer (3), wherein the method comprises the steps of:
(d) providing the bottom layer (3) as a flexible film that is sealingly attached to the body (47) or to the plane rigid cover plate (12) of the disposable cartridge (2) along a circumference (40) of the flexible bottom layer (3), the disposable cartridge (2) thus being devoid of a spacer (5) that is located in the gap (6) for defining a particular distance between said first hydrophobic surface (17') and said second hydrophobic surface (17");
(e) placing the disposable cartridge (2) at a cartridge accommodation site (8) of the base unit (7) of the digital microfluidics system (1);
(f) sealing in the cartridge accommodation site (8) an evacuation space (46) by a gasket (36) or a number of seals (39,39') which are supported by an insertion guide and closing means (25,30), the evacuation space (46) being defined by the flexible bottom layer (3) of the disposable cartridge (8), the uppermost surface (52) of the cartridge accommodation site (8) and the gasket (36) or the number of seals (39,39') with the insertion guide and closing means (25,30); and
(g) creating in the evacuation space (46) an underpressure, which causes the flexible bottom layer (3) of the disposable cartridge (2) that is placed on the cartridge accommodation site (8) to be attracted and spread over the uppermost surface (52) of the cartridge accommodation site (8).

31. The method of claim 30,
wherein defining the gap (6) is carried out by a gasket (36) that is dimensioned to define a height of the gap (6) between the first hydrophobic surface (17') of the bottom layer (3) and the second hydrophobic surface (17") of a disposable cartridge (2).

32. The method of claim 30,
wherein defining the gap (6) is carried out by a rigid spacer (5) on the electrode array (9) of the digital microfluidics system (1) that is dimensioned to define a height of the gap (6) between the first hydrophobic surface (17') of the bottom layer (3) and the second hydrophobic surface (17") of a disposable cartridge (2).

33. The method of claim 30,
wherein the underpressure in the evacuation space (46) is created by a vacuum source (33), which is controlled by the central control unit (14) of the digital microfluidics system (1), and which is linked by a number of vacuum lines (34) to suction holes (35) and/or and a vacuum space (50) for attraction of the flexible bottom layer (3) of the disposable cartridge (2).

34. The method of claim 30,
wherein after manipulating liquid droplets (23) on said first hydrophobic surface (17') by electrowetting and/or analyzing the sample in some of these liquid droplets (23), the disposable cartridge (2) is taken from the cartridge accommodation site (8) of the base unit (7) of the digital microfluidics system (1) and discarded.

35. The disposable cartridge (2) of claim 20, wherein the at least one through hole (19) of the body (47) or of the rigid cover plate (12) is configured as a loading site (41) for transferring processing liquids, reagents or samples into the gap (6).

36. The disposable cartridge (2) of claim 20, wherein the cartridge (2) comprises a top layer (4) that provides the second hydrophobic surface (17") and that is attached to the lower surface (48') of the rigid cover plate (12) of the disposable cartridge (2).

37. The disposable cartridge (2) of claim 19, which further comprises a gasket (36) that is attached to the lower surface (48) of the body (47) or to the lower surface (48') of the rigid cover plate (12), and along a circumference (40) of the flexible bottom layer (3), the gasket (36) defining a particular distance between said first hydrophobic surface (17') and said second hydrophobic surface (17"), when the disposable cartridge (2) is placed over an electrode array (9) of a cartridge accommodation site (8) of the digital microfluidics system (1), if said digital microfluidics system (1) is equipped with suction holes (35) in the electrode array (9), and if the flexible bottom layer (3) is aspirated by said suction holes (35).

38. The disposable cartridge (2) of claim 20, which further comprises a gasket (36) that is attached to the lower surface (48) of the body (47) or to the lower surface (48') of the rigid cover plate (12), and along a circumference (40) of the flexible bottom layer (3), the gasket (36) defining a particular distance between said first hydrophobic surface (17') and said second hydrophobic surface (17"), when the disposable cartridge (2) is placed over an electrode array (9) of a cartridge accommodation site (8) of the digital microfluidics system (1), if said digital microfluidics system (1) is equipped with suction holes (35) in the electrode array (9), and if the flexible bottom layer (3) is aspirated by said suction holes (35).

39. The disposable cartridge (2) of claim 19, wherein the loading sites (41) are selected from a group comprising piercing sites (41'), capillary orifices (41"), and pipetting orifices (41''').

40. The disposable cartridge (2) of claim 20, wherein the loading sites (41) are selected from a group comprising piercing sites (41'), capillary orifices (41"), and pipetting orifices (41''').

41. The disposable cartridge (2) of claim 20, wherein the lower surface (48') of the cover plate (12) is configured as the second hydrophobic surface (17") that at least is permeable to ions.

42. The disposable cartridge (2) of claim 19, wherein the flexible bottom layer (3) is configured as a single layer of a hydrophobic material.

43. The disposable cartridge (2) of claim 20, wherein the flexible bottom layer (3) is configured as a single layer of a hydrophobic material.

44. The disposable cartridge (2) of claim 19, wherein the flexible bottom layer (3) is configured as a single layer of electrically non-conductive material, an upper surface of the flexible bottom layer (3) being treated to be a hydrophobic surface (17).

45. The disposable cartridge (2) of claim 20, wherein the flexible bottom layer (3) is configured as a single layer of electrically non-conductive material, an upper surface of the flexible bottom layer (3) being treated to be a hydrophobic surface (17).

46. The disposable cartridge (2) of claim 19, wherein the flexible bottom layer (3) is configured as a laminate comprising a lower layer and a hydrophobic upper layer, the lower layer being electrically non-conductive.

47. The disposable cartridge (2) of claim 20, wherein the flexible bottom layer (3) is configured as a laminate comprising a lower layer and a hydrophobic upper layer, the lower layer being electrically non-conductive.

48. The disposable cartridge (2) of claim 13 wherein the bottom layer (3) provides a sealing surface.

* * * * *